(12) United States Patent
Wagner

(10) Patent No.: US 9,681,820 B2
(45) Date of Patent: Jun. 20, 2017

(54) SYSTEMS FOR DETECTING A CONDITION

(75) Inventor: Timothy Andrew Wagner, Somerville, MA (US)

(73) Assignee: HIGHLAND INSTRUMENTS, INC., Somerville, MA (US)

( * ) Notice: Subject to any disclaimer, the term of this patent is extended or adjusted under 35 U.S.C. 154(b) by 741 days.

(21) Appl. No.: 13/880,317

(22) PCT Filed: Oct. 19, 2011

(86) PCT No.: PCT/US2011/056841
§ 371 (c)(1),
(2), (4) Date: May 16, 2013

(87) PCT Pub. No.: WO2012/054573
PCT Pub. Date: Apr. 26, 2012

(65) Prior Publication Data
US 2013/0223709 A1    Aug. 29, 2013

Related U.S. Application Data

(60) Provisional application No. 61/405,262, filed on Oct. 21, 2010, provisional application No. 61/432,882, filed on Jan. 14, 2011.

(51) Int. Cl.
*A61B 5/00* (2006.01)
*A61B 5/053* (2006.01)
*A61B 5/03* (2006.01)

(52) U.S. Cl.
CPC ............ *A61B 5/053* (2013.01); *A61B 5/0033* (2013.01); *A61B 5/0051* (2013.01);
(Continued)

(58) Field of Classification Search
CPC ......... A61B 5/053; A61B 5/063; A61B 5/085; A61B 5/068; A61B 5/0033; A61B 5/0051;
(Continued)

(56) References Cited

U.S. PATENT DOCUMENTS 2,830,578 A    4/1958    Degroff et al.
2,838,672 A    6/1958    Leah et al.
(Continued)

FOREIGN PATENT DOCUMENTS

WO    2006/027757 A2    3/2006
WO    2007/149811 A2    12/2007
(Continued)

OTHER PUBLICATIONS

Harting et al., "Regional Differences in Cerebral Edema after Traumatic Brain Injury Identified by Imepdance Analysis", Nov. 27, 2008 (pp. 1-10).*
(Continued)

*Primary Examiner* — Manav Seth
(74) *Attorney, Agent, or Firm* — Adam M. Schoen; Brown Rudnick LLP

(57) ABSTRACT

The invention generally relates to systems for measuring impedance change in order to detect a condition. In certain aspects, the invention provides systems for monitoring tissue and detecting a condition that include at least one energy source, a transduction unit, and a pattern recognition component that compares impedance signatures recorded from the transduction unit with a database of impedance signatures associated with medical conditions.

16 Claims, 2 Drawing Sheets

(52) U.S. Cl.
CPC .......... *A61B 5/0531* (2013.01); *A61B 5/4064* (2013.01); *A61B 5/4884* (2013.01); *A61B 5/6814* (2013.01); *A61B 5/7282* (2013.01); *A61B 5/031* (2013.01)

(58) Field of Classification Search
CPC ... A61B 5/0531; A61B 5/0535; A61B 5/0536; A61B 5/4064; A61B 5/4884; A61B 5/6814; A61B 5/7282; A61B 5/031; A61B 2017/00026
See application file for complete search history.

(56) References Cited

U.S. PATENT DOCUMENTS

| | | | |
|---|---|---|---|
| 3,735,756 A | 5/1973 | Richards et al. | |
| 3,822,708 A | 7/1974 | Zilber | |
| 4,271,848 A * | 6/1981 | Turner | A61N 5/04 607/101 |
| 4,305,402 A | 12/1981 | Katims | |
| 4,403,618 A * | 9/1983 | Turner | A61N 5/04 607/156 |
| 4,503,863 A | 3/1985 | Katims | |
| 4,535,785 A | 8/1985 | van den Honert et al. | |
| 4,611,596 A | 9/1986 | Wasserman | |
| 4,641,633 A | 2/1987 | Delgado | |
| 4,672,951 A | 6/1987 | Welch | |
| 4,709,700 A | 12/1987 | Hyrman | |
| 4,723,536 A | 2/1988 | Rauscher et al. | |
| 4,759,377 A | 7/1988 | Dykstra | |
| 4,805,636 A | 2/1989 | Barry et al. | |
| 4,889,526 A | 12/1989 | Rauscher et al. | |
| 4,923,437 A | 5/1990 | Gordon | |
| 4,989,605 A | 2/1991 | Rossen | |
| 5,014,699 A | 5/1991 | Pollack et al. | |
| 5,061,234 A | 10/1991 | Chaney | |
| 5,113,859 A | 5/1992 | Funke | |
| 5,277,694 A | 1/1994 | Leysieffer et al. | |
| 5,300,093 A | 4/1994 | Koestner et al. | |
| 5,441,532 A * | 8/1995 | Fenn | A61N 5/04 600/412 |
| 5,476,438 A | 12/1995 | Edrich et al. | |
| 5,545,124 A | 8/1996 | Krause et al. | |
| 5,551,953 A | 9/1996 | Lattin et al. | |
| 5,569,591 A | 10/1996 | Kell et al. | |
| 5,575,761 A | 11/1996 | Hajianpour | |
| 5,582,586 A | 12/1996 | Tachibana et al. | |
| 5,713,922 A | 2/1998 | King | |
| 5,738,625 A | 4/1998 | Gluck | |
| 5,767,407 A * | 6/1998 | Sinha | G01N 29/036 702/54 |
| 5,776,170 A | 7/1998 | MacDonald et al. | |
| 5,776,171 A | 7/1998 | Peckham et al. | |
| 5,893,883 A | 4/1999 | Torgerson et al. | |
| 5,895,416 A | 4/1999 | Barreras, Sr. et al. | |
| 5,925,070 A | 7/1999 | King et al. | |
| 5,975,085 A | 11/1999 | Rise | |
| 6,021,348 A | 2/2000 | James | |
| 6,035,236 A | 3/2000 | Jarding et al. | |
| 6,066,084 A | 5/2000 | Edrich et al. | |
| 6,066,163 A | 5/2000 | John | |
| 6,081,744 A | 6/2000 | Loos | |
| 6,091,992 A | 7/2000 | Bourgeois et al. | |
| 6,094,598 A | 7/2000 | Elsberry et al. | |
| 6,102,875 A | 8/2000 | Jones | |
| 6,128,537 A | 10/2000 | Rise | |
| 6,161,048 A | 12/2000 | Sluijter et al. | |
| 6,169,403 B1 | 1/2001 | Hebrank et al. | |
| 6,175,117 B1 * | 1/2001 | Komardin | A61B 6/483 250/363.06 |
| 6,205,356 B1 | 3/2001 | Holcomb | |
| 6,221,908 B1 | 4/2001 | Kilgard et al. | |
| 6,231,527 B1 | 5/2001 | Sol | |
| 6,231,604 B1 | 5/2001 | von Ilberg | |
| 6,234,953 B1 | 5/2001 | Thomas et al. | |
| 6,275,735 B1 | 8/2001 | Jarding et al. | |
| 6,275,737 B1 | 8/2001 | Mann | |
| 6,330,476 B1 | 12/2001 | Ben-Haim et al. | |
| 6,375,666 B1 | 4/2002 | Mische | |
| 6,390,995 B1 | 5/2002 | Ogden et al. | |
| 6,393,325 B1 | 5/2002 | Mann et al. | |
| 6,408,211 B1 | 6/2002 | Powell | |
| 6,432,070 B1 | 8/2002 | Talish et al. | |
| 6,463,328 B1 | 10/2002 | John | |
| 6,468,274 B1 | 10/2002 | Alleyne et al. | |
| 6,491,039 B1 | 12/2002 | Dobak, III | |
| 6,520,903 B1 | 2/2003 | Yamashiro | |
| 6,520,911 B1 | 2/2003 | Wen | |
| 6,535,767 B1 | 3/2003 | Kronberg | |
| 6,536,440 B1 | 3/2003 | Dawson | |
| 6,546,290 B1 | 4/2003 | Shloznikov | |
| 6,567,702 B1 | 5/2003 | Nekhendzy et al. | |
| 6,584,357 B1 | 6/2003 | Dawson | |
| 6,591,138 B1 | 7/2003 | Fischell et al. | |
| 6,594,521 B2 * | 7/2003 | Tucker | A61B 5/0478 600/544 |
| 6,615,080 B1 | 9/2003 | Unsworth et al. | |
| 6,645,144 B1 | 11/2003 | Wen et al. | |
| 6,654,642 B2 | 11/2003 | North et al. | |
| 6,681,131 B2 | 1/2004 | Kandori et al. | |
| 6,685,729 B2 | 2/2004 | Gonzalez | |
| 6,692,490 B1 | 2/2004 | Edwards | |
| 6,721,603 B2 | 4/2004 | Zabara et al. | |
| 6,729,337 B2 | 5/2004 | Dawson | |
| 6,764,498 B2 | 7/2004 | Mische | |
| 6,824,515 B2 | 11/2004 | Suorsa et al. | |
| 6,836,685 B1 | 12/2004 | Fitz | |
| 6,856,824 B1 * | 2/2005 | Wang | A61B 5/0536 378/21 |
| 6,858,000 B1 | 2/2005 | Schukin et al. | |
| 6,866,678 B2 | 3/2005 | Shenderova et al. | |
| 6,871,099 B1 | 3/2005 | Whitehurst et al. | |
| 6,887,239 B2 | 5/2005 | Elstrom et al. | |
| 6,889,085 B2 | 5/2005 | Dawson | |
| 6,921,413 B2 | 7/2005 | Mahadevan-Jansen et al. | |
| 6,934,580 B1 | 8/2005 | Osorio et al. | |
| 6,937,906 B2 | 8/2005 | Terry et al. | |
| 6,941,171 B2 | 9/2005 | Mann et al. | |
| 6,964,643 B2 | 11/2005 | Hovland et al. | |
| 6,970,744 B1 | 11/2005 | Shelchuk | |
| 6,976,998 B2 | 12/2005 | Rizzo et al. | |
| 7,002,790 B2 | 2/2006 | Hossick-Schott et al. | |
| 7,003,352 B1 | 2/2006 | Whitehurst | |
| 7,013,177 B1 | 3/2006 | Whitehurst et al. | |
| 7,058,447 B2 | 6/2006 | Hill et al. | |
| 7,104,947 B2 | 9/2006 | Riehl | |
| 7,120,497 B2 | 10/2006 | Ben-Haim et al. | |
| 7,146,210 B2 | 12/2006 | Palti | |
| 7,173,130 B2 | 2/2007 | Tsien et al. | |
| 7,283,861 B2 | 10/2007 | Bystritsky | |
| 7,395,104 B2 * | 7/2008 | Mouradian | A61B 5/14532 600/345 |
| 7,894,903 B2 | 2/2011 | John | |
| 8,081,304 B2 * | 12/2011 | Furness, III | G01J 3/02 356/71 |
| 8,197,409 B2 | 6/2012 | Foley et al. | |
| 8,277,385 B2 * | 10/2012 | Berka | A61B 5/02433 600/485 |
| 8,535,302 B2 * | 9/2013 | Ben-Haim | A61B 18/1815 606/33 |
| 8,718,758 B2 | 5/2014 | Wagner et al. | |
| 8,862,208 B2 * | 10/2014 | Melnik | A61B 5/0059 600/476 |
| 8,929,979 B2 * | 1/2015 | Wagner | A61N 1/20 601/2 |
| 9,117,133 B2 * | 8/2015 | Barnes | A61B 5/0059 |
| 2001/0051774 A1 | 12/2001 | Littrup et al. | |
| 2003/0009111 A1 * | 1/2003 | Cory | A61B 5/05 600/547 |
| 2004/0131998 A1 | 7/2004 | Marom et al. | |
| 2005/0003380 A1 | 1/2005 | Cohen et al. | |
| 2005/0043726 A1 | 2/2005 | McHale et al. | |
| 2005/0043762 A1 | 2/2005 | Echt et al. | |

(56) References Cited

U.S. PATENT DOCUMENTS

| | | |
|---|---|---|
| 2005/0202489 A1 | 9/2005 | Cho et al. |
| 2006/0004422 A1 | 1/2006 | De Ridder |
| 2006/0017749 A1 | 1/2006 | McIntyre et al. |
| 2006/0247104 A1 | 11/2006 | Grabiner et al. |
| 2006/0257893 A1 | 11/2006 | Takahashi et al. |
| 2007/0060974 A1 | 3/2007 | Lozano |
| 2007/0156180 A1 | 7/2007 | Jaax et al. |
| 2007/0160275 A1* | 7/2007 | Sathyanarayana G06F 17/30265 382/128 |
| 2007/0299370 A1 | 12/2007 | Bystritsky |
| 2008/0039895 A1 | 2/2008 | Fowler et al. |
| 2008/0046053 A1* | 2/2008 | Wagner .................. A61N 1/20 607/116 |
| 2008/0124726 A1 | 5/2008 | Monforte |
| 2008/0228110 A1 | 9/2008 | Berme |
| 2009/0018599 A1 | 1/2009 | Hastings et al. |
| 2009/0240170 A1 | 9/2009 | Rowley et al. |
| 2009/0312644 A1* | 12/2009 | Kosugi ................. A61B 5/0075 600/473 |
| 2010/0070006 A1 | 3/2010 | Wagner et al. |
| 2010/0268287 A1 | 10/2010 | Celnik |
| 2011/0245734 A1 | 10/2011 | Wagner et al. |
| 2011/0275927 A1 | 11/2011 | Wagner et al. |

FOREIGN PATENT DOCUMENTS

| | | |
|---|---|---|
| WO | 2010/009141 A1 | 1/2010 |
| WO | 2010/017392 A2 | 2/2010 |
| WO | 2012/101093 A2 | 8/2012 |
| WO | 2013/054257 A1 | 4/2013 |

OTHER PUBLICATIONS

Advanced Development for Defense Science and Technology, Apr. 5, 2010, 93 pages.

Allen, E.A., et al., Transcranial magnetic stimulation elicits coupled neural and hemodynamic consequences. Science, 2007. 317(5846): p. 1918-21.

Aydin-Abidin, S., et al., Effects of repetitive TMS on visually evoked potentials and EEG in the anesthetized cat: dependence on stimulus frequency and train duration. J Physiol, 2006:443-455.

Benabid, A.L., et al., Deep brain stimulation of the corpus luysi (subthalamic nucleus) and other targets in Parkinson's disease. Extension to new indications such as dystonia and epilepsy. J Neurol, 2001. 248 Suppl 3: p. III37-47.

Bindman LJ, L.O., Redfearn JW., Long-lasting changes in the level of the electrical activity of the cerebral cortex produced by polarizing currents. Nature 1962. 196:584-85.

Bindman, L.J., O.C. Lippold, and J.W. Redfearn, The Action of Brief Polarizing Currents on the Cerebral Cortex of the Rat (1) During Current Flow and (2) in the Production of Long-Lasting after-Effects. J Physiol, 1964. 172:369-82.

Bostock, H., The strength-duration relationship for excitation of myelinated nerve: computed dependence on membrane parameters. J Physiol, 1983. 341: p. 59-74.

Boyden, E.S., et al., Millisecond-timescale, genetically targeted optical control of neural activity. Nat Neurosci, 2005. 8(9):1263-8.

Brice, J. and L. McLellan, Suppression of intention tremor by contingent deep-brain stimulation. Lancet, 1980. 1(8180):1221-2.

Britten, K.H. and R.J. van Wezel, Electrical microstimulation of cortical area MST biases heading perception in monkeys. Nat Neurosci, 1998. 1(1):59-63.

Brown, J.A., et al., Motor cortex stimulation for the enhancement of recovery from stroke: a prospective, multicenter safety study. Neurosurgery, 2006. 58(3): p. 464-73.

Butovas, S. and C. Schwarz, Spatiotemporal effects of microstimulation in rat neocortex: a parametric study using multielectrode recordings. J Neurophysiol, 2003. 90(5):3024-39.

Butson CR, McIntyre CC (2005) Tissue and electrode capacitance reduce neural activation volume during deep brain stimulation. Clin Neurophysiol 116:2490-2500.

Butson, C.R. and C.C. McIntyre, Role of electrode design on the volume of tissue activated during deep brain stimulation. J Neural Eng, 2006. 3(1): p. 1-8.

Butson, C.R. and C.C. McIntyre. Deep brain Stimulation of the the subthalamic nucleus: model-based analysis of the effects of electrode capacitance on the volume of activation. In 2nd International IEEE EMBS Conference on Neural Engineerin. 2005. Arlington, VA: IEEE.

Carbunaru, R. and D.M. Durand, Toroidal coil models for transcutaneous magnetic stimulation of nerves. IEEE Trans Biomed Eng, 2001. 48(4):434-41.

Chew, W.C. and P.N. Sen, Dielectric enhancement due to an electrochemical double layer: thin double layer approximation. J. Chem. Phys., 1982. 77:4683.

Chew, W.C., 1983, Dielectric enhancement and electrophoresis due to electrochmical double layer: A uniform approximation. J Chem Phys. 80(9):4541-4552.

Clement, G.T. and K. Hynynen, A non-invasive method for focusing ultrasound through the human skull. Phys Med Biol, 2002. 47(8):1219-36.

Clement, G.T., et al., A magnetic resonance imaging-compatible, large-scale array for trans-skull ultrasound surgery and therapy. J Ultrasound Med, 2005. 24(8):1117-25.

Clement, G.T., Perspectives in clinical uses of high-intensity focused ultrasound. Ultrasonics, 2004. 42(10):1087-93.

Cohen, D. and B.N. Cuffin, Developing a more focal magnetic stimulator. Part 1: some basic principles. Journal of Clinical Neurophysiology, 1991. 8:102-111.

Cohen, L.G., et al., Effects of coil design on delivery of focal magnetic stimulation. Technical considerations. Electroencephalogr Clin Neurophysiol, 1990. 75(4):350-7.

Cohen, M.R. and W.T. Newsome, What electrical microstimulation has revealed about the neural basis of cognition. Curr Opin Neurobiol, 2004. 14(2):169-77.

Connor, C.W. and K. Hynynen, Patterns of Thermal Deposition in the Skull During Transcranial Focused Ultrasound Surgery. IEEE Trans Biomed Eng, 2004. 51(10):1693-1706.

Connor, C.W., G.T. Clement, and K. Hynynen, A unified model for the speed of sound in cranial bone based on genetic algorithm optimization. Phys Med Biol, 2002. 47(22):3925-44.

Cramer, S.C., et al., Use of functional MRI to guide decisions in a clinical stroke trial. Stroke, 2005. 36(5):e50-2.

Deuschl, G., et al., Deep brain stimulation: postoperative issues. Mov Disord, 2006. 21 Suppl 14:S219-37.

Di Lazzaro, V., et al., The physiological basis of transcranial motor cortex stimulation in conscious humans. Clin Neurophysiol, 2004. 115(2):255-66.

Diamond, A. and J. Jankovic, The effect of deep brain stimulation on quality of life in movement disorders. J Neurol Neurosurg Psychiatry, 2005. 76(9):1188-93.

Diokno, A.C., P.B. Leu, and D.B. Konstandt, A simplified method of implanting a neuromodulator device. J Urol, 2003. 169(4):1466-9.

Dissado, L.A., A fractal interpertation of the dielectric response of animal tissues. Phys. Med. Biol., 1990. 35(11):1487-1503.

Ditterich, J., M.E. Mazurek, and M.N. Shadlen, Microstimulation of visual cortex affects the speed of perceptual decisions. Nat Neurosci, 2003. 6(8):891-8.

Donald I. McRee, Howard Wachtel, Pulse Microwave Effects on Nerve Vitality, Radiation Research, vol. 91, No. 1, (1982):212-218.

Duck, F.A., Medical and non-medical protection standards for ultrasound and infrasound. Prog Biophys Mol Biol, 2007. 93(1-3):176-91.

Durand, D. and M. Bikson, Suppression and control of epileptiform activity by electrical stimulation: a review. Proceedings of the IEEE, 2001. 89(7):1065-1082.

Eaton, H., Electric field induced in a spherical volume conductor from arbitrary coils: applications to magnetic stimulation and MEG. Medic Biol Eng Comput, 1992:433-440.

Esselle, K. and M. Stuchly, Neural stimulation with magnetic fields: analysis of induced electrical fields. IEEE Transactions on Biomedical Engineering, 1992. 39:693-700.

(56) References Cited

OTHER PUBLICATIONS

Extended European Search Report for Application No. 12826175.7 dated Mar. 9, 2015 (6 pages).
Extended Supplementary European Search Report for Application No./Patent No. 12752660.6 dated Jul. 9, 2014 (6 pages).
Fields, J.A., et al., Neuropsychological and quality of life outcomes 12 months after unilateral thalamic stimulation for essential tremor. J Neurol Neurosurg Psychiatry, 2003. 74(3):305-11.
Fixman, M., Charged macromolecules in external fields. I. The sphere. J Chem Phys, 1980. 72(9):5177-5186.
Fixman, M., Thin double layer approximation for electrophoresis and dielectric respons. J Chem Phys, 1982. 78(3):1483-1492.
FralexTherapeutics, Fralex Provides Update on Relief Trial. 2008: Toronto, (Downloaded from the Internet May 25, 2013).
Fregni, F. and A. Pascual-Leone, Technology insight: noninvasive brain stimulation in neurology-perspectives on the therapeutic potential of rTMS and tDCS. Nat Clin Pract Neurol, 2007. 3(7):383-93.
Fry WJ, W.V., Tucker D, Fry FJ, Physical factors involved in ultrasonically induced changes in living systems: I. Identification of non-temperature effects. J Acoust Soc Am 1950. 22:867-876.
Fry, E.J., An ultrasonic projector design for a wide range of research applications. Rev Sci Instrum, 1950. 21(11):940-1.
Fry, W. J., Electrical Stimulation of Brain Localized Without Probes—Theoretical Analysis of a Proposed Method, J Acoust Soc AM 44(4):919-31 (1968).
Fry, W.J., Use of intense ultrasound in neurological research. Am J Phys Med, 1958. 37(3):143-7.
Gabriel, C., S. Gabriel, and E. Corthout, The dielectric properties of biological tissues: I. Literature survey. Phys Med Biol, 1996. 41(11):2231-49.
Miranda, P.C., M. Hallett, and P.J. Basser, The electric field induced in the brain by magnetic stimulation: a 3-D finite-element analysis of the effect of tissue heterogeneity and anisotropy. IEEE Trans Biomed Eng, 2003. 50(9):1074-85.
Miranda, P.C., M. Lomarev, and M. Hallett, Modeling the current distribution during transcranial direct current stimulation. Clin Neurophysiol, 2006. 117(7):1623-9.
Montalibet, A., et al., Electric current generated by ultrasonically induced Lorentz force in biological media. Med. Biol. Eng. Comput., 2001, vol. 39:15-20.
Mouchawar, G., et al., Magnetic Stimulation of excitable tissue: calculation of induced eddy currents with a three-dimensional finite-element model. IEEE Transactions on Magnetics, 1993. 29(6):3355-3357.
Murasugi, C.M., C.D. Salzman, and W.T. Newsome, Microstimulation in visual area MT: effects of varying pulse amplitude and frequency. J Neurosci, 1993. 13(4):1719-29.
Mushahwar, V.K. and K.W. Horch, Selective activation of muscle groups in the feline hindlimb through electrical microstimulation of the ventral lumbo-sacral spinal cord. IEEE Trans Rehabil Eng, 2000. 8(1):11-21.
Nadeem, M., et al., Computation of electric and magnetic stimulation in human head using the 3-D impedance method. IEEE Transactions on Biomedical Engineering, 2003. 50(7):900-907.
Nagarajan, S. and D.M. Durand, Analysis of magnetic stimulation of a concentric axon in a nerve bundle. IEEE Transactions on Biomedical Engineering, 1995. 42(9):926-933.
Nagarajan, S., D.M. Durand, and E.N. Warman, Effects of induced electric fields on finite neuronal structures: a simulation study. IEEE Transactions on Biomedical Engineering, 1993. 40(11):1175-1188.
Nagarajan, S., et al. Magnetic stimulation of finite neuronal structures. in Annual International Conference of the IEEE Engineering in Medicine and Biology Society. 1991: IEEE.
Nathan, S.S., et al., Determination of current density distributions generated by electrial stimulation of the human cerebral cortex. Electroencephalogr Clin Neurophysiol, 1993. 86(3):183-92.
Neri Accornero et al., 'Visual evoked potentials modulation during direct current cortical polarization', Experimental Brain Research, Oct. 19, 2006, vol. 178, No. 2, pp. 261-266.
Nichols, M.J. and W.T. Newsome, Middle temporal visual area microstimulation influences veridical judgments of motion direction. J Neurosci, 2002. 22(21):9530-40.
Northstar Neuorsciences, Northstar Neuroscience Announces Primary Endpoint Results of EVEREST Clinical Trial. 2008: Seattle, (Downloaded from the Internet May 25, 2013).
Norton, 2003, Can ultrasound be used to stimulate nerve tissue, BioMedical Engineering OnLine 2(6):1-9.
O'Brien, W.D., Jr., Ultrasound-biophysics mechanisms. Prog Biophys Mol Biol, 2007. 93(1-3):212-55.
Pascual-Leone, A., D. Bartres-Faz, and J.P. Keenan, Transcranial magnetic stimulation: studying the brain-behaviour relationship by induction of 'virtual lesions'. Philos Trans R Soc Lond B Biol Sci, 1999. 354(1387):1229-38.
Perlmutter, J.S. and J.W. Mink, Deep Brain Stimulation. Annu Rev Neurosci, 2006:229-257.
Pernot, M., et al., In vivo transcranial brain surgery with an ultrasonic time reversal mirror. J Neurosurg, 2007. 106(6):1061-6.
Plonsey R, Heppner DB, (1967), Considerations of quasi-stationarity in electrophysiological systems. Bull Math Biophys 29:657-664.
Priori, A., Brain polarization in humans: a reappraisal of an old tool for prolonged non-invasive modulation of brain excitability. Clin Neurophysiol, 2003. 114(4):589-95.
Prochazka, A., V.K. Mushahwar, and D.B. McCreery, Neural prostheses. J Physiol, 2001. 533(Pt 1):99-109.
Purpura, D.P. and J.G. McMurtry, Intracellular Activities and Evoked Potential Changes During Polarization of Motor Cortex. J Neurophysiol, 1965. 28:166-85.
Ramos-Estebanez, C., et al., Visual phosphene perception modulated by subthreshold crossmodal sensory stimulation. J Neurosci, 2007. 27(15):4178-81.
Ranck, J.B., Jr., Which elements are excited in electrical stimulation of mammalian central nervous system: a review. Brain Res, 1975. 98(3):417-40.
Rattay, F., et al., Mechanisms of Electrical Stimulation with Neural Prostheses. Neuromodulation, 2003. 6(1):42-56.
Rezai, A.R., et al., Deep brain stimulation for Parkinson's disease: surgical issues. Mov Disord, 2006. 21 Suppl 14:S197-218.
Romo, R., et al., Somatosensory discrimination based on cortical microstimulation. Nature, 1998. 392(6674):387-90.
Roth, B.J., Mechanisms for electrical stimulation of excitable tissue. Critical Reviews in Biomedical Engineering, 1994. 22(3-4):253-305.
Rousche, P. and R. Normann, Chronic Intracortical Microstimulation (ICMS) of Cat Sensory Cortex Using the Utah Intracortical Electrode Array. IEEE Trans Rehabil Eng, 1999. 7(1):56-68.
Rush, S. and D.A. Driscoll, Current distribution in the brain from surface electrodes. Anesth Analg, 1968. 47(6):717-23.
Rutten, W.L.C., et al., The influence of ultrasound and ultrasonic focusing on magnetic and electric peripheral nerve stimulation., in Advances in Magnetic Stimulation: Mathematical modeling and clinical applications, J. Nilsson, M. Panizza, and F. Grandori, Editors. 1996: Pavia, Italy, (p. 152).
Salzman, C.D., et al., Microstimulation in visual area MT: effects on direction discrimination performance. J Neurosci, 1992. 12(6):2331-55.
Salzman, C.D., K.H. Britten, and W.T. Newsome, Cortical microstimulation influences perceptual judgements of motion direction. Nature, 1990. 346(6280):174-7.
Saypol, J.M., et al., A theoretical comparison of electric and magnetic stimulation of the brain. Annals of Biomedical Engineering, 1991. 19(3):317-28.
Schmidt, E.M., et al., Feasibility of a visual prosthesis for the blind based on intracortical microstimulation of the visual cortex. Brain, 1996. 119 ( Pt 2):507-22.
Schwartzbaum, J.S., Electrophysiology of taste, feeding and reward in lateral hypothalamus of rabbit. Physiol Behav, 1988. 44(4-5):507-26.
Schwarz, G.J., A Theory of the Low Fequency Dielectric Dispersion of Colloidal Particles in Electrolyte Solutions, J Phys Chem, 1962. 66:2636.

(56) References Cited

OTHER PUBLICATIONS

Scivill, I., A.T. Barker, and I.L. Freeston, Finite element modelling of magnetic stimulation of the spine. Proceedings 18th annual international conference of the IEEE engineering in medicine and biology society, 1996:393-394.
Seidemann, E. and W.T. Newsome, Effect of spatial attention on the responses of area MT neurons. J Neurophysiol, 1999. 81(4):1783-94.
Seidemann, E., et al., Color signals in area MT of the macaque monkey. Neuron, 1999. 24(4):911-7.
Shupak, N.M., et al., Exposure to a specific pulsed low-frequency magnetic field: a double-blind placebo-controlled study of effects on pain ratings in rheumatoid arthritis and fibromyalgia patients. Pain Res Manag, 2006. 11(2):85-90.
Spiegel, R.J., et al., Measurement of small mechanical vibrations of brain tissue exposed to extremely-low-frequency electric fields. Bioelectromagnetics, 1986. 7(3):295-306.
Stecker, M.M., T. Patterson, and B.L. Netherton, Mechanisms of electrode induced injury. Part 1: theory. Am J Electroneurodiagnostic Technol, 2006. 46(4):315-42.
Stojanovic, M.P. and S. Abdi, Spinal cord stimulation. Pain Physician, 2002. 5(2):156-66.
Stoney, S.D., Jr., W.D. Thompson, and H. Asanuma, Excitation of pyramidal tract cells by intracortical microstimulation: effective extent of stimulating current. J Neurophysiol, 1968. 31(5):659-69.
Tehovnik, E.J. and W.M. Slocum, Microstimulation of V1 affects the detection of visual targets: manipulation of target contrast. Exp Brain Res, 2005. 165(3):305-14.
Tehovnik, E.J., Electrical stimulation of neural tissue to evoke behavioral responses. J Neurosci Methods, 1996. 65(1):1-17.
Terzuolo, C.A. and T.H. Bullock, Measurment of Imposed Voltage Gradient Adequate to Modulate Neuronal Firing. Proc Natl Acad Sci U S A, 1956. 42(9):687-694.
Thickbroom, G.W., Transcranial magnetic stimulation and synaptic plasticity: experimental framework and human models. Exp Brain Res, 2007. 180(4):583-93.
Thomas, A.W., D.J. Drost, and F.S. Prato, Human subjects exposed to a specific pulsed (200 microT) magnetic field: effects on normal standing balance. Neurosci Lett, 2001. 297(2):121-4.
Tofts, P.S., The distribution of induced currents in magnetic stimulation of the nervous system. Physical Medicine and Biology, 1990. 35:1119-1128.
Tranchina, D. and C. Nicholson, A model for the polarization of neurons by extrinsically applied electric fields. Biophys J, 1986. 50(6):1139-56.
Traub RD, (1977), Motorneurons of different geometry and the size principle. Biol Cybern 25:163-176.
Troster, A.I., et al., Neuropsychological deficits in essential tremor: an expression of cerebello-thalamo-cortical pathophysiology? Eur J Neurol, 2002. 9(2):143-51.
Tyler, W.J., et al., Remote excitation of neuronal circuits using low-intensity, low-frequency ultrasound. PLoS One, 2008. 3(10):e3511.
Ueno, S., T. Tashiro, and K. Harada, Localised stimulation of neural tissues in the brain by means of a paired configuration of time-varying magnetic fields. J. Appl. Phys., 1988. 64:5862-5864.
Wagner T, Valero-Cabre A, Pascual-Leone A, (2007), Noninvasive Human Brain Stimulation. Annu Rev Biomed Eng., 7.1:19.1-19.39.
Wagner TA, Zahn M, Grodzinsky AJ, Pascual-Leone A, (2004), Three-dimensional head model simulation of transcranial magnetic stimulation. IEEE Trans Biomed Eng 51:1586-1598.
Wagner, T., et al., Biophysical foundations underlying TMS: Setting the stage for an effective use of neurostimulation in the cognitive neurosciences. Cortex 45, 2008:1025-1034.
Wagner, T., et al., Transcranial direct current stimulation: a computer-based human model study. Neuroimage, 2007. 35(3):1113-24.
Wagner, T., et al., Transcranial magnetic stimulation and brain atrophy: a computer-based human brain model study. Exp Brain Res 189, 2008:539-550.
Wagner, T., et al., Transcranial magnetic stimulation and stroke: a computer-based human model study. Neuroimage, 2006. 30(3):857-70.
Wagner, T., Field distributions within the human cortex induced by transcranial magnetic stimulation, in EECS. 2001, Massachusetts Institute of Technology: Cambridge., Chapters 1 and 2, (126 pages).
Warman, E.N., W.M. Grill, and D. Durand, Modeling the effects of electric fields on nerve fibers: determination of excitation thresholds. IEEE Trans Biomed Eng, 1992. 39(12):1244-54.
Wichmann, T. and M.R. Delong, Deep brain stimulation for neurologic and neuropsychiatric disorders. Neuron, 2006. 52(1):197-204.
Wininger, F.A., J.L. Schei, and D.M. Rector, Complete optical neurophysiology: toward optical stimulation and recording of neural tissue. Appl Opt, 2009. 48(10):D218-24.
Wobschall, D., Bilayer Membrane Elasticity and Dynamic Response. Journal of Colloid and Interface Science, 1971. 36(3):385-396.
Wobschall, D., Voltage Dependence of Bilayer Membrane Capacitance. Journal of Colloid and Interface Science, 1972. 40(3):417-423.
Wongsarnpigoon, A. and W.M. Grill, Computational modeling of epidural cortical stimulation. J Neural Eng, 2008. 5(4):443-54.
Zangen, A., et al., Transcranial magnetic stimulation of deep brain regions: evidence for efficacy of the H-coil. Clin Neurophysiol, 2005. 116(4):775-9.
Gabriel, S., R.W. Lau, and C. Gabriel, The dielectric properties of biological tissues: II. Measurements in the frequency range 10 Hz to 20 GHz. Phys Med Biol, 1996. 41(11):2251-69.
Gabriel, S., R.W. Lau, and C. Gabriel, The dielectric properties of biological tissues: III. Parametric models for the dielectric spectrum of tissues. Phys Med Biol, 1996. 41(11):2271-93.
Gielen, F. Deep Brain Stimulation: Current Practice and Challenges for the Future. In 1st International IEEE EMBS Conference on Neural Engineering. 2003. Capri Island, Italy: IEEE.
Graziano, M.S., C.S. Taylor, and T. Moore, Complex movements evoked by microstimulation of precentral cortex. Neuron, 2002. 34(5):841-51.
Grill, W.M., et al., Temporal excitation properties of paresthesias evoked by thalamic microstimulation. Clin Neurophysiol, 2005. 116(5):1227-34.
Grill, W.M., S.E. Norman, and R.V. Bellamkonda, Implanted neural interfaces: biochallenges and engineered solutions. Annu Rev Biomed Eng, 2009. 11:1-24.
Grosse, C., Permitivity of suspension of charged particles in electrolyte solution. J. Chem. Phys., 1987. 91:3073.
Gusev, V., et al., Imaging With the Ultrasonic Vibration Potential: A Theory for Current Generation. Ultrasound in Med. & Biol., 2005. vol. 31, No. 2:273-278.
Haar, G.t., Accoustic Surgery: Bursts of focused ultrasound energy three orders of magnitude more intense than diagnostic ultrasound are emerging as a noninvasive option for treating cancer and other medical procedures., Physics Today, 2001:29-34.
Hart FX, Toll RB, Berner NJ, Bennett NH, (1996), The low frequency dielectric properties of octopus arm muscle measured in vivo. Phys Med Biol 41:2043-2052.
Hart, F.X. and W.R. Dunfree, In vivo measurements of low frequency dielectric spectra of a frog skeletal muscle. Phys. Med. Biol., 1993. 38:1099-1112.
Hatanaka, N., et al., Input-output organization of jaw movement-related areas in monkey frontal cortex. J Comp Neurol, 2005. 492(4):401-25.
Heller L, Hulsteyn DBv, (1992), Brain stimulation using electromagnetic sources: theoretical aspects. Biophysical Journal 63:129-138.
Hinch, E.J., et al., Dielectric response of a dilute suspension of spheres with thin double layers in an asymmetric electrolyte. J Chem Soc, Faraday Tans., 1983. 80:535-551.
Holdefer, R.N., R. Sadleir, and M.J. Russell, Predicted current densities in the brain during transcranial electrical stimulation. Clin Neurophysiol, 2006. 117(6):1388-97.

(56) References Cited

OTHER PUBLICATIONS

Hole, S. and T. Ditchi, Non-destructive Methods for Space Charge Distribution Measurements: What are the Differences? IEEE Embs, 2003. 10(4):670-677.

Hsiao, I. and V. Lin, Improved coil design for functional magnetic stimulation of expiratory muscles. IEEE Trans Biomed Eng, 2001. 48(6):684-694.

Hsu KH and D. DM., A 3-D differential coil design for localized magnetic stimulation. IEEE Trans Biomed Eng, 2001. 48(10):1162-8.

International Search Report for PCT/US2013/053006 dated Mar. 18, 2010 (3 pages).

Jones KE, Bawa P, (1997), Computer simulation of the responses of human motoneurons to composite 1A EPSPS: effects of background firing rate. J Neurophysiol 77:405-420.

Kanai, R., et al., Frequency-dependent electrical stimulation of the visual cortex. Curr Biol, 2008. 18(23):1839-43.

Kanner, A.M., Deep brain stimulation for intractable epilepsy: which target and for which seizures? Epilepsy Curr, 2004. 4(6):231-2.

Kaufman, E.F. and A.C. Rosenquist, Efferent projections of the thalamic intralaminar nuclei in the cat. Brain Res, 1985. 335(2):257-79.

Khachaturian, M.H., et al., Focal reversible deactivation of cerebral metabolism affects water diffusion. Magn Reson Med, 2008. 60(5):1178-89.

Khraiche, M.L., et al., Ultrasound induced increase in excitability of single neurons. Conf Proc IEEE Eng Med Biol Soc, 2008. 2008: p. 4246-9.

Kleim, J.A., T.A. Jones, and T. Schallert, Motor enrichment and the induction of plasticity before or after brain injury. Neurochem Res, 2003. 28(11):1757-69.

Komissarow, L., et al., Triple stimulation technique (TST) in amyotrophic lateral sclerosis. Clin Neurophysiol, 2004. 115(2):356-60.

Kraus, K.H., et al., The use of a cap-shaped coil for transcranial magnetic stimulation of the motor cortex. J Clin Neurophysiol, 1993. 10(3):353-62.

Kumar, K., C. Toth, and R.K. Nath, Deep brain stimulation for intractable pain: a 15-year experience. Neurosurgery, 1997. 40(4):736-46; Discussion 746-7.

Larkin, J., et al., Combined electric field and ultrasound therapy as a novel anti-tumour treatment. European Journal of Cancer 41 (2005):1339-1348.

Lemay, M.A., et al., Endpoint forces obtained during intraspinal microstimulation of the cat lumbar spinal cord—experimental and biomechanical model results. in IEEE 28th Annual Northeast Bioengineering Conference, 2002, IEEE.

Li, D.L., et al. Finite element analysis of transcranial electrical stimulation for intraoperative monitoring. in Bioengineering Conference, Proceedings of the IEEE 31st Annual Northeast 2005, IEEE.

Lin, V., I. Hsiao, and V. Dhaka, Magnetic coil design considerations for functional magnetic stimulation. IEEE Trans Biomed Eng, 2000. 47(5):600-610.

Lomber, S.G., The advantages and limitations of permanent or reversible deactivation techniques in the assessment of neural function. J Neurosci Methods, 1999. 86(2):109-17.

Lozano, A.M., et al., Deep brain stimulation for Parkinson's disease: disrupting the disruption. Lancet Neurol, 2002. 1(4):225-31.

Luber, B., et al., Remediation of sleep-deprivation-induced working memory impairment with fMRI-guided transcranial magnetic stimulation. Cereb Cortex, 2008. 18(9):2077-85.

McCreery D, Agnew W, (1990), Neuronal and axonal injury during functional electrical stimulation; a review of the possible mechanisms. In: Annual International Conference of the IEEE Engineering in Medicine and Biology Society, p. 1489:IEEE.

McCreery, D., et al., Accessing the Tonotopic Organization of the Ventral Cochlear Nucleus by Intranuclear Microstimulation. IEEE Trans Rehabil Eng, 1998. 6(4):391-399.

McCreery, D., et al., Charge Density and Charge Per Phase as Cofactors in Neural Injury Induced by Electrical Stimulation. IEEE Trans Biomed Eng, 1990. 37(10):996-1001.

McIntyre, C.C. and W.M. Grill, Excitation of central nervous system neurons by nonuniform electric fields. Biophys J, 1999. 76(2):878-88.

McIntyre, C.C. and W.M. Grill, Extracellular stimulation of central neurons: influence of stimulus waveform and frequency on neuronal output. J Neurophysiol, 2002. 88(4):1592-604.

McIntyre, C.C., et al., Cellular effects of deep brain stimulation: model-based analysis of activation and inhibition. J Neurophysiol, 2004. 91(4):1457-69.

McIntyre, C.C., et al., Electric field and stimulating influence generated by deep brain stimulation of the subthalamic nucleus. Clin Neurophysiol, 2004. 115(3):589-95.

McNeal DR, (1976), Analysis of a model for excitation of myelinated nerve. IEEE Trans Biomed Eng 23:329-337.

McRee, D.I. and H. Wachtel, Elimination of microwave effects on the vitality of nerves after blockage of active transport. Radiat Res, 1986. 108(3):260-8.

McRee, D.I. and H. Wachtel, Pulse microwave effects on nerve vitality. Radiat Res, 1982. 91(1):212-8.

McRee, D.I. and H. Wachtel, The effects of microwave radiation on the vitality of isolated frog sciatic nerves. Radiat Res, 1980. 82(3):536-46.

Medtronic, Activa® PC Implant Manual, Medtronic, Editor. 2007, Medtronic: Minneapolis.

Mihran, R.T., et al., Temporally-Specific Modification of Myelinated Axon Excitability In Vitro Following a Single Ultrasound Pulse. Ultrasound in Med. & Biol., 1990, vol. 16, No. 3:297-309.

Miocinovic, S. and W.M. Grill, Sensitivity of temporal excitation properties to the neuronal element activated by extracellular stimulation. J Neurosci Methods, 2004. 132(1):91-9.

\* cited by examiner

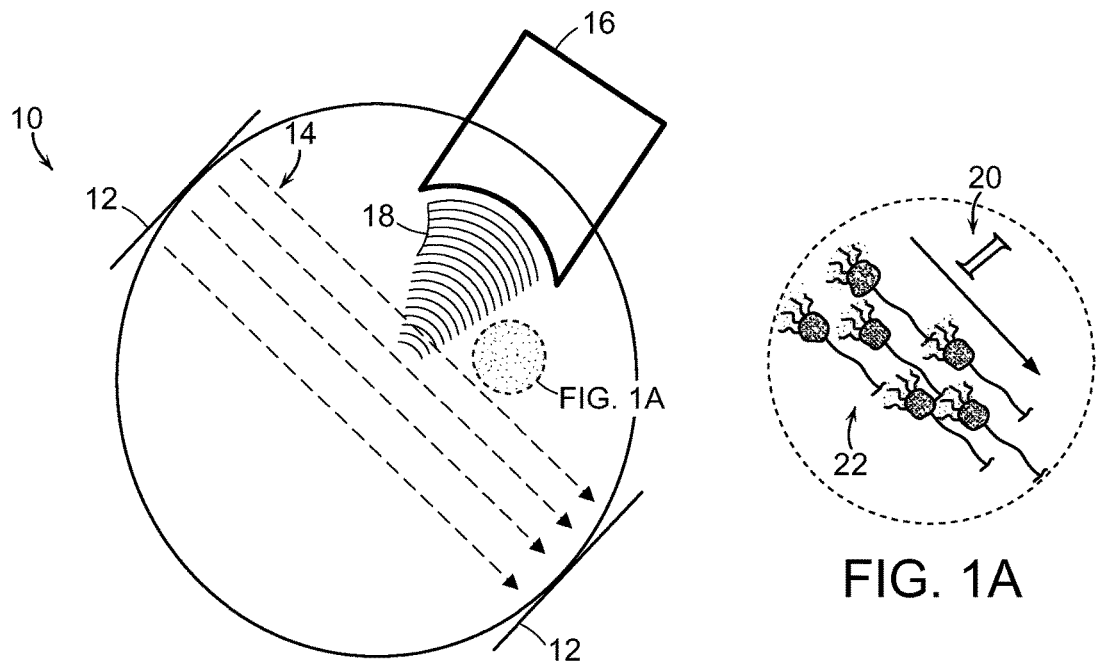
FIG. 1
FIG. 1A
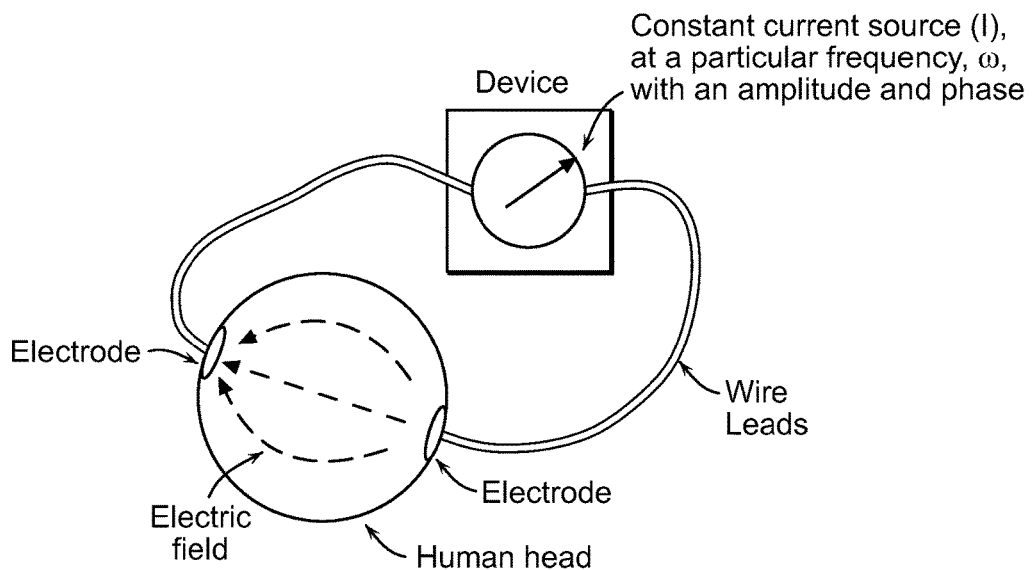
FIG. 3

SYSTEMS FOR DETECTING A CONDITION

RELATED APPLICATION

The present application is a 35 U.S.C. §371 national phase application and claims the benefit of and priority to PCT/US11/56841, filed Oct. 19, 2011, which claims the benefit of and priority to U.S. provisional application Ser. Nos. 61/432,882, filed Jan. 14, 2011, and 61/405,262, filed Oct. 21, 2010, the content of each of which is incorporated by reference herein in its entirety.

FIELD OF THE INVENTION

The invention generally relates to systems for measuring impedance change in order to detect a condition.

BACKGROUND

There has been a rapid increase in the application of devices to diagnose a variety of pathologies, such as neuropathologies. Diagnostic techniques can rely on imaging methods, metabolic tests, and other methods to investigate changes in cells, tissues, organs, and systems. Diagnostic techniques may be applied invasively, e.g., by performing surgery to remove a portion of the skull and implanting electrodes in a specific location within brain tissue to characterize the tissue, or non-invasively, e.g., investigating changes in tissues with scalp surface based electrodes.

SUMMARY

The invention recognizes that measuring impedance change over a period of time in a particular tissue can be used for detecting a condition within that tissue. Every tissue has different electrical impedance. When the tissue is subject to trauma (e.g., a traumatic brain injury) or afflicted with a condition (e.g., a stroke, or cancer), the impedance of that tissue changes over time, and the impedance change is unique to the condition that afflicts the tissue, i.e., a unique impedance signature. For example, brain tissue that has been subject to a traumatic brain injury produces a different impedance signature than brain tissue that has been afflicted with cancer. Similarly, brain tissue that has been subject to a mild traumatic brain injury produces a different impedance signature than brain tissue that has been subject to a severe traumatic brain injury. Systems of the invention make use of these unique impedance signatures for determining injury types (e.g., hemorrhagic vs. ischemic strokes) and injury severity.

In certain aspects, the invention provides systems for monitoring tissue and detecting a condition that include at least one energy source, a transduction unit, and a pattern recognition component that compares impedance signatures recorded from the transduction unit with a database of impedance signatures associated with medical conditions. In certain embodiments, the impedance signature is based on changes of the spectral content of the impedance measurements. In certain embodiments the energy source could also serve as the transduction unit. Systems of the invention may be used to detect or diagnosis any condition within tissue. Exemplary conditions include a heart attack, a stroke (e.g., ischemic stroke or hemorrhagic stroke), a cancer, or a traumatic brain injury (e.g., a concussion). In certain embodiments, the energy source and the transduction unit are integrated with each other. In other embodiments, the system is integrated with an imaging system. In other embodiments, the system is integrated with additional diagnostic equipment, such as devices to measure intracranial pressure (ICP) or an Electroencephalogram (EEG) device.

In addition to electrical impedance, other electromagnetic properties, chemical properties, optical properties, thermodynamic properties, mechanical properties, and/or a combination of properties thereof may be investigated as the basis for diagnosing a condition. Characteristics can be tracked as a function of: time, position, tissue type, applied energy spectral content, applied energy phase, applied energy direction (vector information), applied energy magnitude, and/or type/amount/composition of energy applied.

In certain embodiments, multiple tissue properties can be investigated simultaneously and correlated to and/or used to predict diagnose a condition (such as for example correlating the change in intracranial pressure (ICP) with tissue electromagnetic impedance to diagnose or characterize traumatic brain injury), or one property can be used to predict another tissue property important in diagnosing or characterizing a disease (such as for example using an electromagnetic impedance to predict ICP and the extent of an injury in the brain).

Any type of energy known in the art may be used with methods of the invention. Exemplary energy types include electromagnetic, chemical, optical, thermal, mechanical, or a combination thereof. In certain embodiments, the type of energy is mechanical energy, such as that produced by an ultrasound device. In certain embodiments, the ultrasound device includes a focusing element so that the mechanical field may be focused. In other embodiments, the mechanical energy is combined with an additional type of energy, such as chemical, optical, electromagnetic, or thermal energy.

In other embodiments, the type of energy is electrical energy, such as that produced by placing at least one electrode in or near the tissue. In certain embodiments, the electrical energy is focused, and focusing may be accomplished based upon placement of electrodes. In other embodiments, the electrical energy is combined with an additional type of energy, such as mechanical, chemical, optical, electromagnetic, or thermal energy. In certain embodiments, the electric energy is produced by an electric source, such as an electrode. In certain embodiments, the electrode may be a component of a second system selected from the group consisting of: EEG, EKG, EOG, ERG, and ENG. In certain embodiments, the energy could be applied from multiple electrodes, which could be also be used in the transduction process (simultaneously or at varying time points the electrodes could be used for one role or the other).

Another aspect of the invention provides a system for monitoring tissue and detecting a condition that includes an electric source that produces an electric field, an electrical transduction unit, a pattern recognition component that compares impedance signatures recorded from the transduction unit with a database of impedance signatures associated with medical conditions; and a helmet that houses at least the electric source or transduction unit.

Another aspect of the invention provides a system for monitoring tissue and detecting a condition that includes a noninvasive transcranial energy source, a transduction unit, and a pattern recognition component that compares impedance signatures recorded from the transduction unit with a database of impedance signatures associated with medical conditions.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 1 is a view of one embodiment of an apparatus for applying energy to biological tissue constructed in accordance with the principles of the present disclosure.

FIG. 1A is a magnified view of a portion of FIG. 1.

FIG. 3 is a schematic showing part of an exemplary device that can be used to measure impedance change in tissue.

DETAILED DESCRIPTION

Figure 2:
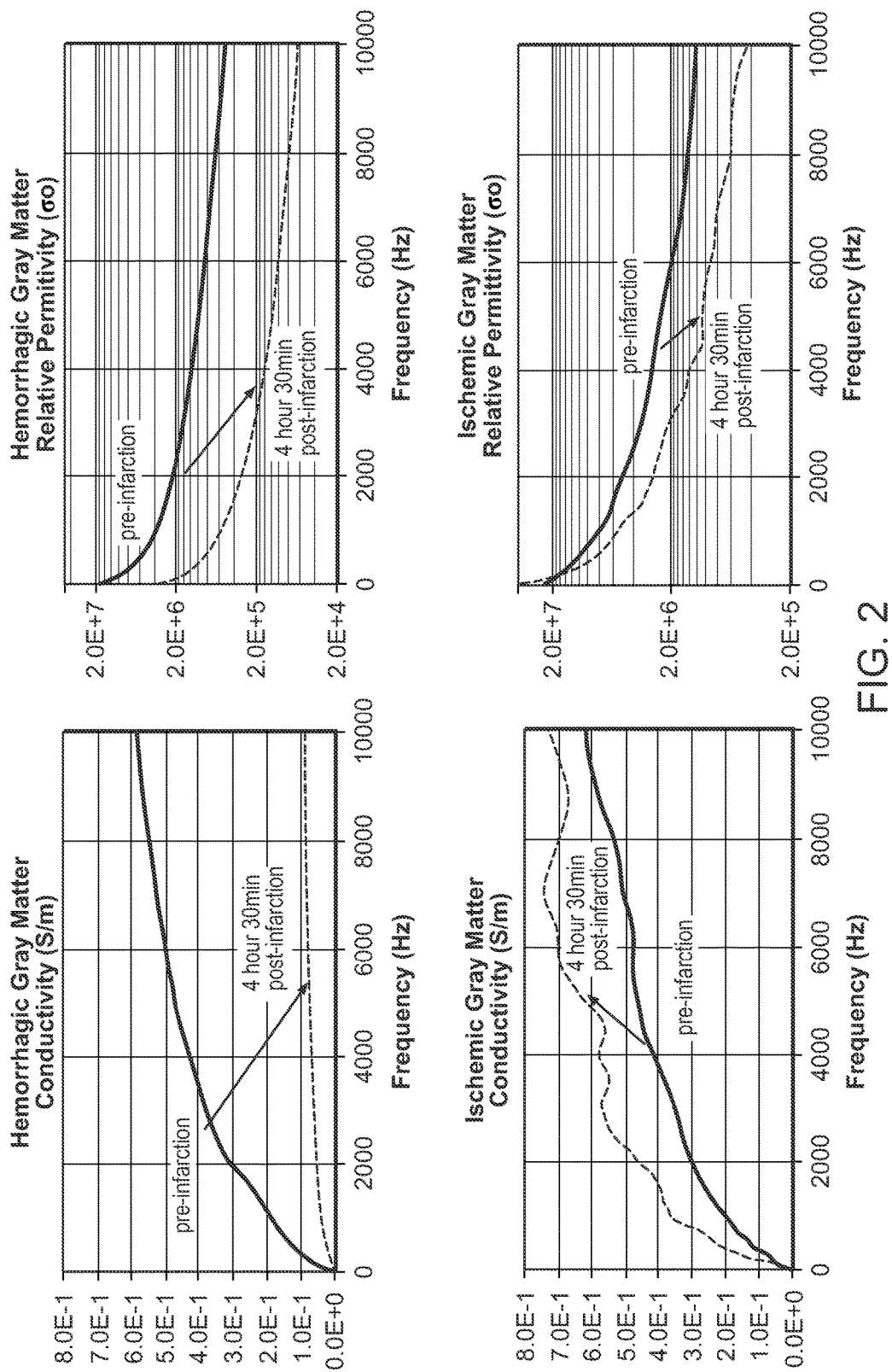
FIG. 2 is a set of graphs showing that potential differences in tissue conductivity and permittivity are dependent on type and severity of stroke.

The invention generally relates to systems for measuring change in tissue properties in order to detect a condition. Systems of the invention provide that at least one type of energy is applied to at least one tissue from at least one energy source; the characteristics/distribution of energy in the tissues is measured, recorded, and processed; and the way in which the energy is changed by the tissue is analyzed. The way in which the tissue changes the characteristics of the energy can be used to characterize the tissue and diagnose potential pathological processes ongoing in the tissue. Tissue(s) can change energy as a function of: time, position, tissue type, applied energy spectral content (frequency), applied energy phase, applied energy direction (vector information), applied energy magnitude, and/or type/amount/composition of energy applied. Additionally, the way in which the energy is changed can also be correlated to and/or used to predict: tissue type, tissue distribution, tissue vitality, tissue age, tissue injury, tissue pathology, abnormal elements in the tissue, tissue metabolism, and/or biological processes ongoing in the tissue. The measurements and energy applications may be at any location on the body using noninvasive techniques, in the body using invasive techniques, and/or in an organ using invasive techniques (in any combination).

In certain aspects, systems of the invention include at least one energy source, a transduction unit, and a pattern recognition component that compares energy signatures recorded from the transduction unit with a database of energy signatures associated with medical conditions. Systems of the invention may be applied to any injury/pathology type, where an injury type results in specific tissue characteristic changes with time (such as for example, certain aspects systems of the invention provide for tracking impedance changes (such as in magnitude and phase as a function of frequency) with time which are correlated with a spectral signature of an injury/pathology type). Furthermore the method can be used to describe the distribution (size, shape, and/or location), severity, and/or progression (as function of time and extent) of the injury/pathology. The individual sub-components or combinations of subcomponents of the device/methods could also be used, such as one could used the methods/device to characterize tissue independent of disease diagnosis (such as for example one might use the methods/devices described herein to characterize tissue for a treatment or tissue stimulation method, such as those described in Wagner et al. (U.S. patent application number 2008/0046053), the content of which is incorporated by reference herein in its entirety.

Energy Sources

Exemplary components for applying energy to tissue are shown in Wagner et al. (U.S. patent application number 2008/0046053), the content of which is incorporated by reference herein in its entirety.

Any type of energy known in the art may be used with methods of the invention, such as electromagnetic, mechanical, thermal, optical, and/or chemical energy (applied individually or in any combination).

In certain embodiments, the type of energy is mechanical energy, such as that produced by an ultrasound device. In certain embodiments, the ultrasound device includes a focusing element so that the mechanical field may be focused. The mechanical field may be pulsed, time varying, or pulsed a plurality of time with each pulse being for a different length of time. The mechanical field may be generated with low field strengths (such as with the same intensities already used for diagnostic ultrasound imaging) In other embodiments, the mechanical energy is combined with an additional type of energy, such as chemical, optical, electromagnetic, or thermal energy.

In other embodiments, the type of energy is electrical energy, such as that produced by placing at least one electrode in or near the tissue. In certain embodiments, the electrical energy is focused, and focusing may be accomplished based upon placement of electrodes. The electric field may be pulsed, time varying, pulsed a plurality of time with each pulse being for a different length of time, or time invariant. The electric field may be generated with low field strengths (such as from constant current sources in $mA/cm^2$ or lower level intensities (or comparable low voltages if the current source is not considered fixed)). In other embodiments, the electrical energy is combined with an additional type of energy, such as mechanical, chemical, optical, electromagnetic, or thermal energy.

In particular embodiments, the energy is a combination of an electric field and a mechanical field. The electric field may be pulsed, time varying, pulsed a plurality of time with each pulse being for a different length of time, or time invariant. The mechanical field may be pulsed, time varying, or pulsed a plurality of time with each pulse being for a different length of time. In certain embodiments, the electric field and/or the mechanical field is focused.

Turning now to FIG. 1, which illustrates an exemplary embodiment of an apparatus 10 to apply energies to tissue(s) in accordance with the present disclosure. An initial source electric field 14 results in a current in the tissue. The electric field 14 is created by an electric source, such as a current or voltage source. Electrodes 12 are applied to the scalp and generate a low magnitude electric field 14 over a large brain region. While electrodes 12 are used and applied to the scalp in this exemplary embodiment, it is envisioned that the electrodes may be applied to a number of different areas on the body including areas around the scalp. It is also envisioned that one electrode may be placed proximal to the tissue being stimulated and the other distant, such as one electrode on the scalp and one on the thorax. It is further envisioned that electric source could be mono-polar with just a single electrode, or multi-polar with multiple electrodes (such as multiple electrodes applied using a 10-20 system common to an EEG system, or hundreds of electrodes forming a grid along the scalp). Similarly, the electric source may be applied to tissue via any medically acceptable medium. It is also envisioned that means could be used where the electric source does not need to be in direct contact with the tissue, such as for example, inductive magnetic sources where the entire tissue region is placed within a large solenoid generating magnetic fields or near a coil generating magnetic fields, where the magnetic fields induce electric currents in the tissue. It is also possible multiple electrodes could be used (with multiple ground locations, a single ground location, or no ground (i.e., a floating ground)).

The electric source may be direct current (DC) or alternating current (AC) and may be applied inside or outside the tissue of interest. Additionally, the source may be time varying. Similarly, the source may be pulsed and may be comprised of time varying pulse forms. The source may be an impulse. Also, the source according to the present disclosure may be intermittent. The electric field source could also work as a component in the imaging process.

A mechanical source such as an ultrasound source 16 is applied on the scalp and provides concentrated acoustic energy 18, i.e., mechanical field to a focused region of neural tissue, affecting a smaller area of tissue (such as a group of neurons 22) and alters the tissue permittivity relative to the applied electric field 14, and thereby generating the altered current 20 (whereby the altered energy fields could be further used to investigate and characterize the tissues and diagnose disease). While the example herein demonstrates the acoustic energy focused relative to the electrical energy, applications where both are unfocused is also possible (and any mixture of focused and unfocused energies is contemplated). The mechanical source may be any acoustic source such as an ultrasound device. Generally, such device may be a device composed of electromechanical transducers capable of converting an electrical signal to mechanical energy such as those containing piezoelectric materials, a device composed of electromechanical transducers capable of converting an electrical signal to mechanical energy such as those in an acoustic speaker that implement electromagnets, a device in which the mechanical source is coupled to a separate mechanical apparatus that drives the system, or any similar device capable of converting chemical, plasma, electrical, nuclear, or thermal energy to mechanical energy and generating a mechanical field.

Furthermore, the mechanical field could be generated via an ultrasound device, such as an ultrasound transducer that could be used for imaging tissue. The mechanical field may be coupled to tissue via a bridging medium, such as a container of saline to assist in the focusing or through gels and/or pastes which alter the acoustic impedance between the mechanical source and the tissue. The mechanical field may be time varying, pulsed, an impulse, or may be comprised of time varying pulse forms. It is envisioned that the mechanical source may be applied inside or outside of the tissue of interest.

There are no limitations as to the frequencies that can be applied via the mechanical source, however, exemplary mechanical field frequencies range from the sub kHZ to 1000s of MHz. Additionally, multiple transducers providing multiple mechanical fields with similar or differing frequencies, and/or similar or different mechanical field waveforms may be used—such as in an array of sources like those used in focused ultrasound arrays. Similarly, multiple varied electric fields could also be applied. Additionally, there are no limitations as to the frequencies that can be applied via the electrical source, however, exemplary electrical field frequencies range from the DC to 100s of kHz (for electromagnetic impedance changes in tissue in the alpha dispersion band where complex impedance changes can be significant).

The combined fields, electric and mechanical, may be controlled intermittently to generate specific energy patterns in bandwidths particular to a disease being investigated. For example, the device may produce a periodic signal at a fixed frequency, or high frequency signals at a pulsed frequency (such as where energies are applied simultaneously to cause cellular stimulation, such as detailed in Wagner et al. (U.S. patent application number 2008/0046053), while simultaneously at least one of the energies is used in the process to diagnose or characterize a pathology). The ultrasound source may be placed at any location relative to the electrode locations, i.e., within, on top of, below, or outside the same location as the electrodes as long as components of the electric field and mechanical field are in the same region. The locations of the sources should be relative to each other such that the fields intersect relative to the tissue and cells to be investigated.

The apparatus and method where the electromagnetic and acoustic source are coupled, and devices such as those explained in (U.S. patent application number 2008/0046053), generate capacitive currents via impedance alterations, which can be significant in magnitude, especially in the presence of low frequency applied electric fields (this additional property of using combined energies can be used in the exploration of the tissues properties explained below). A displacement current is generated by the modification of the permittivity in the presence of the electric field and provides an additional signal that can be investigated for disease diagnosis and characterization. In addition to the main permittivity change that occurs in the tissues, a conductivity change could also occur in the tissue, which secondarily alters the ohmic component of the currents. In a further embodiment, the displacement current generation and altered ohmic current components may combine and be investigated for disease diagnosis and characterization.

Although the process which combines two energy fields, such as an electrical and mechanical field, to generate an altered current may be accomplished at any frequency of the applied electric field, the method in an exemplary embodiment is applied with lower frequency applied electric fields due to the fact the permittivity magnitudes of tissues, as high as or greater than $10^8$ times the permittivity of free space, and the electric field penetration depths are highest for low frequency applied electric fields. Higher frequency applied electric fields may be less desirable as they will require greater radiation power to penetrate the tissue and/or a more pronounced mechanical source for permittivity alteration to achieve the same relative tissue permittivity change, i.e., at higher applied electric field frequencies the permittivity of the tissue is lower and as such would need a greater overall perturbation to have the same overall change in permittivity of a tissue as at a lower frequency. Applied electric field frequencies in the range of DC to approximately 100,000 Hz frequencies are advantageous due to the high tissue permittivity in this frequency band and the high penetration depth for biological tissues at these frequencies. In this band, tissues are within the so called 'alpha dispersion band' where relative tissue permittivity magnitudes are maximally elevated (i.e., as high as or greater than $10^8$ times the permittivity of free space). Frequencies above approximately 100,000 to 1,000,000 Hz for the applied electric fields are still applicable for the method described in generating displacement currents for the stimulation of biologic cells and tissue.

In the higher range (above 1,000,000 Hz), the magnitude of the applied electric field needs to be increased, or the method used to alter the permittivity relative to the applied electric field increased to bring about a greater permittivity change, relative to the tissue's permittivity magnitude for the applied electric field frequency. The technique could still be applied in more superficial applications in a noninvasive manner or via an invasive method. Higher frequency applied electric fields, above 1,000,000 to 100,000,000 Hz, could be also used in generating displacement currents for the stimulation of biologic cells and tissue.

Although the specific example of FIG. 1 demonstrates a method to provide energy through multiple sources, the diagnostic methods in this disclosure can be accomplished with: just one of the energies individually, multiple energies applied and the energies analyzed individually to investigate different aspects of the tissue change (e.g., where mechanical changes and electromagnetic changes are analyzed individually), multiple energies are applied and analyzed together, where multiple energies are applied and the impact of energy modification (e.g., displacement current generation) is used as the basis to investigate tissue change, multiple energies applied for one purpose (such as tissue stimulation) and one individual energy is simultaneously applied to investigate tissue change, and/or in any permutation (multiple energy sources of the same energy source may also be applied, such as with varying characteristics of source frequency, phase, amplitude, timing, direction (energy vector properties)).

Systems and methods of the invention may include a focusing element. The focusing element may focus either the electric field, the mechanical field, or both simultaneously (or any energy being applied). In certain embodiments, the focusing element focuses both the electric field and the mechanical field. The focusing element may be composed of inert material (such as a lens) or active material. The focusing element may be designed such that it is acoustically and/or electrically matched and/or coupled with the electric field or mechanical field that transmits through them (for example, one could use the matching and/or coupling to limit the attenuation and/or modification (i.e., dispersion effects, phase shifting, beam focus, etc) of the mechanical field or electric field), and/or to alter the mechanical fields properties such as to be ideal for stimulation, for example through matching the acoustic impedances of the sources with the material of the focusing interface and/or the tissues.

The focusing element could also have its electromagnetic properties matched and/or altered relative to the electrical source to facilitate the energy application alteration (such as by matching all of the electric impedances of the relevant parts through the appropriately designed focusing element). In certain embodiments, the focusing element is filled with a fluid through which the mechanical field can travel unimpeded where the electrode is an electrically conducting thin latex like membrane (connected to a voltage or current source) that is coated in a conducting ultrasound gel at the tissue-interface boundary through which the ultrasound energy can transmit. The fluid above the membrane could be non-conducting such as to prevent the spread of the electric field into the fluid (such that electrical energy focused towards the underlying tissue does not spread to the fluid above contained within the interface component). This concept of matching the properties may be applied in any permutation (via the focusing element and/or the tissues and/or with any potential sources, including the primary electrical source(s) and/or any means for altering the tissue electromagnetic properties (i.e., the ultrasound/mechanical field and/or source(s), chemical agent and/or source(s), thermal field and/or source(s), optical field/beam and/or source(s), and/or secondary electromagnetic field and/or source(s))).

As the electric field is to be coupled to the mechanical field, the focusing element itself can be comprised of materials, active and/or inert, that serve as a bridging medium, thus creating an interface, and thereby appropriately couple and/or match the acoustic characteristics and/or electromagnetic properties between the mechanical source and/or fields (or other means for altering electromagnetic characteristics) and/or the electric source and/or fields and/or the tissues to augment the stimulation. This can be done for example, by having the focusing element at least in part capable of: actively and/or passively matching and/or altering the electrical and acoustic impedances of the interface to the electrical and mechanical field frequencies that are tuned for the diagnostic measurement being made, and/or actively and/or passively matching and/or altering the electrical and acoustic impedances of the interface to the sources such that the sources themselves are matched and more efficient in use, and/or altering its interface materials such that the speed of sound and/or light is changed in them so that the fields that impinge on the tissue to be investigated in the targeted tissue, and/or altering the dispersive properties of its interface materials so the mechanical and/or electrical fields have a controllable frequency dependent behavior in the materials such as to tune the field frequencies to diagnostic measure and bandwidth being investigated, and/or making its interface materials capable of filtering the fields as to tune the fields to diagnostic measure, and/or altering the densities of the interface materials altering the transmission of fields through the interface to maximize diagnostic information that can be captured from applied energy, and/or allowing its interface materials to shift the phase of individual fields thereby restructuring the waveforms that impinge on the tissue, and/or altering the focus or targeting of the fields to apply energy to different tissue targets, and/or altering the orientation of the vector field components thereby potentially altering the energy response of the tissue being investigated (for example exploring anisotropic tissue properties), and/or altering the magnitude of the fields to maximize diagnostic information that is determined from the measurements, and/or altering the field waveform dynamics/shapes to focus on the timing of the diagnostic measure being made, etc.

Any material and/or sub-property in a focusing and/or interface element could be actively or passively modified to focus the fields and/or alter the field properties of the energy applied as part of this diagnostic procedure. For example the impedance to energy (e.g., electrical, magnetic, electromagnetic, acoustic, thermal, optical, etc.), penetration depth of energy, velocity of propagation of energy, phase velocity of energy, group velocity of energy, reflection properties to energy, refraction properties to energy, scattering properties to energy, diffraction properties to energy, interference properties to energy, absorption properties to energy, attenuation properties to energy, birefringence properties to energy, refractive properties to energy, charge density (e.g., free, paired, ionic, etc.), conductivity to energy, fluid content, ionic concentrations, electrical permittivity, electrical conductivity, electrical capacitance, magnetic permeability, elasticity properties, stress properties, strain properties, combined properties to multiple energy types (e.g., electroacoustic properties, electrothermal properties, electrochemical properties, etc), piezoelectric properties, piezoceramic properties, condensation properties, magnetic properties, stiffness properties, viscosity properties, gyrotropic properties, uniaxial properties, anisotropic properties, bianisotropic properties, chiral properties, solid state properties, optical properties, ferroelectric properties, ferroelastic properties, density, compressibility properties, kinematic viscosity properties, specific heat properties, Reynolds number, Rayleigh number, Damkohler number, Brinkman number, Nusselt Schmidt number, number, Peclet number, bulk modulus, Young's modulus, Poisson's ratio, Shear Modulus, Prandtl number, Adiabatic bulk modulus, entropy, enthalpy, pressure, heat transfer coefficient, heat capacity, friction coefficients, diffusivity, temperature, thermal conductivity, weight, dimensions, position, velocity, acceleration, shape, convexity mass, molecular concentration of any material and/or group of materials could be modified to focus the fields and/or alter the field properties for stimulation (materials can be synthetic, biological, natural, and solids, gasses, liquids, and/or plasmas). Additional examples of methods and/or systems of focusing and or modifying the properties of a field for this diagnostic procedure include using elements such as lenses (of any type (e.g., optical, electromagnetic, electrical, magnetic, acoustic, thermal, chemical, etc) which can have their focusing properties modified or tuned); using waveguides; using fiber optics; phase matching between materials; impedance matching between materials; using reflection, refraction, diffraction, interference, and/or scattering methods.

Energy may be applied in a single application in time (such as for comparing a tissue to a typical tissue value stored in a database), or in applying energy more times over a period of time (such as for analyzing how a tissue property changes with time, for example as would be used in identifying a typical impedance signature of impedance changes in a tissue as a function of time).

Transduction Unit/System to Measure Applied Energy Characteristics Across Tissue/Processing Unit The process for diagnosing a disease or characterizing the disease as a function of the way in which the applied energy is affected by the tissue requires measuring characteristics of the energy field across the tissue (such as for example measuring tissue impedances (both amplitude and phase) as a function of frequency, time, and position to diagnose a disease). Dependent on the energy type, numerous methods can be employed to make contact (direct (e.g., implanted electrode) and/or indirect(inductive)) with the tissue(s) under investigation and serve as the recording point of the energy distribution in the tissue(s), such as for example using: body surface electrodes (polarizable or non-polarizable electrodes) such as those as for example an electrode places on the scalp (solid metal or flexible electrodes) to record an electromagnetic voltage or current signal; implantable microelectrodes to record an electromagnetic voltage or current signal; needle electrodes to record an electromagnetic voltage or current signal; capacitive or conductive electrodes; any material with known electromagnetic properties in which an electrical contact can be made between the tissue and the electrical system exploring the electromagnetic characteristics of the tissue; an acoustic transduction mechanism; microphone systems; pressure meters; scales; piezo-electric materials; strain gauges; linear variable differential transformers; optoelectronics; semiconductor materials whose properties changes with pressure (or any energy interaction, such as optical, mechanical, electrical, thermal energy); fluid based interfaces where changes in fluid properties can be used to measure energy characteristics; elements whose resistance, inductance, capacitance, and or impedance changes with pressure (or any energy interaction, such as optical, mechanical, electrical, thermal energy); optical materials whose characteristics thermometers changes with pressure (or any energy interaction, such as optical, mechanical, electrical, thermal energy); chemical biosensors; displacement measurement sensors; resistive sensors; bridge circuits; inductive sensors; capacitive sensors; piezoelectric sensors; temperature sensors; thermocouples; thermistors; radiation thermometers; fiber optic temperature sensors; optical sensors; mechanical sensors; thermal sensors; electrical sensors; radiation sensors; combined sensors (e.g., electrochemical sensors); liquid and or gas filled pressure sensors; and/or devices and/or mechanisms such as those described in Medical Instrumentation Application and Design by John G. Webster (Feb. 3, 2009) or Principles of Applied Biomedical Instrumentation by L. A. Geddes and L. E. Baker (1989) (such as ones normally used to record bio-potentials, but now used to record energy distributions that are artificially applied to the system(the sensors can also be used to record biologically produced bio-potentials)), the references which are incorporated by reference herein in their entirety. Furthermore any element used to provide energy (such as those explained above in the Energy sources section) can be used in an inverse manner to record energy.

Generally, the method/device used to interface with tissue (s) is implemented in a manner where the energy changes they are recording are transduced to an electrical signal (such as with transduction processes described in Medical Instrumentation Application and Design by John G. Webster (Feb. 3, 2009) or Principles of Applied Biomedical Instrumentation by L. A. Geddes and L. E. Baker (1989)). These components are then connected with a means to condition, amplify, and/or process the signal, for example, this can be an electrical device that includes components such as an amplifier system(s), a filtering system(s), and/or a processing unit(s). Amplification systems may consist of a preamplifier, which would exist near/on the tissue interface, and potentially a second amplification system used after the system is filtered. The filtering could be applied before and/or after amplification. This can involve individual components and/or an integrated unit(s). The system could be comprised of mechanical, thermal, electrical (digital and/or analog), optical, and/or chemical components. The signal could be processed in an analog or digital format (which would be digitally sampled after the signal was conditioned (and amplified if necessary)). For all of the electrical signals recorded from the tissue, the process could be accomplished via measurements made relative to: a single ground point, multiple ground locations, or no ground (a floating ground).

While an electrical device will be preferred in most typical uses (and primarily used as the base examples herein), a device based on mechanical components or analogs to electrical components could be fabricated for use in some environments (such as for example a device based on mechanical components (such as springs, pneumatics, and other mechanical components) might be useful for synchronous use during MRI imaging, where electrical noise from an electrical device and/or components might need to be removed)). Furthermore, any energy signal (electromagnetic, mechanical, thermal, optical, chemical) can be recorded, processed, and/or analyzed with a system based on electromagnetic, mechanical, thermal, optical, and/or chemical means.

The recorded energy signal can be processed to simply give a value of the energy characteristic being measured, or analyzed along multiple levels and analyzed as functions of: time, position, tissue being investigated, applied energy spectral content (frequency), applied energy phase, applied energy direction (vector information), applied energy magnitude, and/or type/amount/composition of energy applied. Additionally, the way in which the energy is changed can also be correlated to and/or used to predict: tissue type, tissue distribution, tissue vitality, tissue age, tissue injury (including type of injury in tissue, extent of injury, shape of injury, progression of injury), tissue pathology (including type of pathology in tissue, extent of pathology, shape of pathology, progression of pathology), abnormal elements in the tissue, chemical distribution in tissue, ionic distribution in tissue, cellular distribution in tissue, tissue metabolism, and/or biological processes ongoing in the tissue.

The recorded energy characteristics in the tissue being investigated can be compared to the characteristics of the source energy itself and/or used to determine characteristics of the tissue being investigated. Such as for example, electrical energy can be applied to tissue(s) from an electrical source, such as a voltage controlled or current controlled source. This corresponding current or voltage driving the system can be used to determine the tissue impedance based on a non fixed signal which is recorded from an electrical sensor and through an amp meters and/or voltage meters (or power measurements)). For example, if energy is provided with a controlled current source but the voltage is allowed to vary depending on the tissue impedance, the tissue impedance can be determined based on the voltage necessary to drive the system (with the fixed voltage) where the impedance is simply a function of the measured voltage signal divided by the applied controlled current signal. To focus on the frequency dependence of the impedance, the impedance calculations can be done in the complex space (such as where impedance calculations can be done with methods such as those described in Electric Circuits by James W. Nilsson and Susan Riedel (2010)) where the impedance calculations can be tracked in magnitude and phase in the complex space- and the energy would be applied in fixed frequency steps spanning the band of interest. Ultimately, current, voltage, and/or total power could be used in this process, through calculations such as those explained in (Electric Circuits by James W. Nilsson and Susan Riedel (2010)), where the transduction unit serves as a complex impedance meter. When exploring inductance based energy sources, the methods to determine energy distributions will have to take into account potential voltmeter (if used) corrections that would be needed, as shown in (Romer, R., What Do Voltmeters Measure—Farady Law in a Multiply Connected Region. Am. J. Phys., 1982. 50(12): p. 1089-1093.) the content of which is incorporated by reference herein in its entirety.

Additionally, while a specific example based on electromagnetic tissue impedance as the material property that can be tracked/analyzed to diagnose a condition in a tissue is described herein, the process for investigating the tissue can be based on numerous energy types (electromagnetic, thermal, optical, mechanical, and/or thermal), and based on numerous tissue material properties that act on the energy, for example this includes a tissue's (and/or group of tissues'): impedance to energy (e.g., electromagnetic, mechanical (which includes sonic (a.k.a. acoustic) energy), thermal, optical, etc.), impedance to energy as a function of energy frequency, impedance to energy as a function of energy direction/orientation (i.e., vector behavior), impedance to energy as a function of time (such as from the last application of energy or at a specific time point (such as could be relative to a tracked process), impedance to energy as a function of tissue position and/or tissue type, impedance to energy as a function of energy phase, impedance to energy as a function of energy temporal behavior, impedance to energy as a function of other energy type applied and/or the characteristics of the other energy type (such as for a combined energy application where an additional energy type(s) is applied to modify the impedance of one tissue relative to other energy types that are applied), impedance to energy as function of tissue velocity (for tissue(s) moving relative to the energy and/or the surrounding tissue(s) moving relative to a targeted tissue), impedance to energy as a function of tissue temperature, impedance to energy as a function of physiological processes ongoing in tissue(s), impedance to energy as a function of pathological processes ongoing in tissue(s), and/or impedance to energy as a function of applied chemicals (applied directly or systemically).

The relationship between individual impedance properties to an energy or energies (such as for example the relationship that electrical conductivity, electrical permittivity, and/or electrical permeability have to each other) can be the material property that can be tracked/analyzed to diagnose a condition in a tissue. Other material properties can be tracked/analyzed to diagnose a condition in a tissue, including: the velocity of propagation of energy in the tissue(s), phase velocity of energy in the tissue(s), group velocity of energy in the tissue(s), reflection properties to energy of the tissue(s), refraction properties to energy of the tissue(s), scattering properties to energy of the tissue(s), diffraction properties to energy of the tissue(s), interference properties to energy of the tissue(s), absorption properties to energy of the tissue(s), attenuation properties to energy of the tissue(s), birefringence properties to energy of the tissue(s), and refractive properties to energy of the tissue(s). This can further include a tissue(s'): charge density (e.g., free, paired, ionic, etc.), conductivity to energy, fluid content, ionic concentrations, electrical permittivity, electrical conductivity, electrical capacitance, electrical inductance, magnetic permeability, inductive properties, resistive properties, capacitive properties, impedance properties, elasticity properties, stress properties, strain properties, combined properties to multiple energy types (e.g., electroacoustic properties, electrothermal properties, electrochemical properties, etc), piezoelectric properties, piezoceramic properties, condensation properties, magnetic properties, stiffness properties, viscosity properties, gyrotropic properties, uniaxial properties, anisotropic properties, bianisotropic properties, chiral properties, solid state properties, optical properties, ferroelectric properties, ferroelastic properties, density, compressibility properties, kinematic viscosity properties, specific heat properties, Reynolds number, Rayleigh number, Damkohler number, Brinkman number, Nusselt Schmidt number, number, Peclet number, bulk modulus, Young's modulus, Poisson's ratio, Shear Modulus, Prandtl number, Adiabatic bulk modulus, entropy, enthalpy, pressure, heat transfer coefficient, heat capacity, friction coefficients, diffusivity, porosity, mechanical permeability, temperature, thermal conductivity, weight, dimensions, position, velocity, acceleration, shape, convexity mass, molecular concentration, acoustic diffusivity, and/or coefficient of nonlinearity.

When multiple energy types are applied, they can be analyzed individually or in combination, as shown for example in Wagner et al. (U.S. patent application Ser. No. 13/216,282). The energy types can be analyzed independent of each other (such as where acoustic and electrical energy are applied to the tissue at separate locations and the fields are not interacting at the sites of application), or as combined energies (such as where acoustic and electrical energy interact in a targeted region of tissue).

In some embodiments, the transduction/analysis unit can be integrated with the energy source. For example, the electrodes that apply the energy (from an electrical source) can also be used as the element to record the energy once it is applied to the tissue (where the electrical source can be integrated with the transduction and analysis system). Multiple transduction mechanisms (such as an electrode array) could also be used. Additionally, the energy source and recording units can be alternated in function (and/or be used for multiple functions such as if multiple electrodes are being used, electrodes could apply energy at one frequency while simultaneously recording the energy distributions in the tissue at another frequency). The method/systems described herein can also be accomplished with a separate source and recording systems (even though they can be comprised of the same mechanisms (e.g., the methods and devices described as energy sources could also be used as energy recording elements if used in an inverse manner, such as for example electrodes could be used to record energy signals and serve as the source of energy)).

Pattern Recognition Unit/Advanced Processing

The pattern recognition unit is communicating with the electrical transduction unit to receive the obtained tissue characteristic (such as an impedance signature) and analyze the received signature by comparing it to a database of reference signatures. A match between the obtained signature and a reference signature in the database provides a diagnosis of the condition. The severity of the condition is also determined based upon which reference signature matches the obtained signature. The database could be as simple as containing one single criteria relative to the measurements to multiple permutations and combinations of criteria relative to the measurements to be used to diagnose as disease.

Furthermore, one can calculate the predicted energy field distribution expected in the tissues (and at the location where the fields will be recorded from the recording elements and transduction units) and compare it to the energy recordings to characterize the tissue under investigation. Such as for example, one could predict an expected electromagnetic field from impedance values known from healthy tissue (or an earlier tissue sample, such as from a prior recording), where the prediction of the field distributions could be made from methods described in Wagner et al. (U.S. patent application Ser. No. 13/216,282), and then one could compare the predicted field distribution (as predicted at the location of the recording elements) to what is recorded at the transduction unit to further determine how the tissue being investigated has deviated from the healthy state (or earlier recorded state). For example one could predict a electromagnetic field distribution, at a particular applied field frequency, based on a solution to Poison's Equation in the tissue, as a function of the tissue anatomy/distribution (such as could be determined from an earlier MRI from a patient, or a standard model developed to represent healthy tissue/systems based on prerecorded tissue values and general anatomy characteristics of a system under study) or as a function of standard model (such as multi-sphere model designed to represent the subject under study) and known electromagnetic impedance of the tissue and the source energy properties, and then compare the predicted field distributions with those that are recorded. These type of comparisons could be used to determine changes in the energy fields, such as a change(s) in an energy fields': magnitude, position, dynamic behavior (i.e., behavior as a function of time), static behavior, behavior in the frequency domain, phase information, orientation/direction of energy fields (i.e., vector behavior), duration of energy application (in single or multiple sessions), type/amount/composition of energy (such as for electromagnetic energy, the energy stored in the electric field, the magnetic field, or the dissipative current component (such as could be described with a Poynting Vector)), and/or the relationship between multiple energy types (e.g., magnitude, timing, phase, frequency, direction, and/or duration relationship between different energy types (such as for example for an electromechanical energy (i.e., energy provided from mechanical field source, such as ultrasound device, and an electrical field source, such as an electrode) pulse, the amount of energy stored in an acoustic energy pulse compared with that stored in an electric pulse)). Furthermore this comparison could be used to predict or describe characteristics of the tissue being studied, including tissue characteristics such as: tissue type, tissue distribution, tissue vitality, tissue age, tissue injury (including type of injury in tissue, extent of injury, shape of injury, progression of injury), tissue pathology (including type of pathology in tissue, extent of pathology, shape of pathology, progression of pathology), abnormal elements in the tissue, chemical distribution in tissue, ionic distribution in tissue, cellular distribution in tissue, tissue metabolism, and/or biological processes ongoing in the tissue.

The pattern recognition unit can include computer storage. The storage can be in the form of one or more computer-readable mediums having data and/or executable instructions (also called computer programs, code, or software) stored thereon or therein. The software is for performing various computer-implemented processing operations such as any or all of the various operations, functions, and capabilities described herein. In certain embodiments, the processing operations include accessing a database of reference signatures and comparing the obtained signature to the reference signatures in the database.

The term "computer-readable medium" is used herein to include any medium capable of storing data and/or storing or encoding a sequence of computer-executable instructions or code for performing the processing operations described herein. The media and code can be those specially designed and constructed for the purposes of the invention, or can be of the kind well known and available to those having ordinary skill in the computer and/or software arts. Examples of computer-readable media include computer-readable storage media such as: magnetic media such as fixed disks, floppy disks, and magnetic tape; optical media such as Compact Disc-Read Only Memories ("CD-ROMs") and holographic devices; magneto-optical media such as floptical disks; memory sticks "flash drives" and hardware devices that are specially configured to store and execute program code, such as Application-Specific Integrated Circuits ("ASICs"), Programmable Logic Devices ("PLDs"), Read Only Memory ("ROM") devices, and Random Access Memory ("RAM") devices. Examples of computer-executable program instructions or code include machine code, such as produced by a compiler, and files containing higher level code that are executed by a computer using an interpreter. For example, an embodiment of the invention may be implemented using Java, C++, or other programming language and development tools. Additional examples of instructions or code include encrypted code and compressed code. Other embodiments of the invention can be implemented in whole or in part with hardwired circuitry in place of, or in combination with, program instructions/code.

The software can run on a local computer, a dedicated chip/microprocessor unit, and/or a remote computer accessed via network connections. The computer may be a desktop computer, a laptop computer, a tablet PC, a cellular telephone, a Blackberry, or any other type of computing device. The computer machine can include a CPU, a ROM, a RAM, an HDD (hard disk drive), an HD (hard disk), an FDD (flexible disk drive), an FD (flexible disk), which is an example of a removable recording medium, a display, an I/F (interface), a keyboard, a mouse, a scanner, and a printer. These components are respectively connected via a bus and are used to execute computer programs described herein. Here, the CPU controls the entire computer machine. The ROM stores a program such as a boot program. The RAM is used as a work area for the CPU. The HDD controls the reading/writing of data from/to the HD under the control of the CPU. The HD stores the data written under the control of the HDD. The FDD controls the reading/writing of data from/to the FD under the control of the FDD. The FD stores the data written under the control of the FDD or causes the computer machine to read the data stored in the FD. The removable recording medium may be a CD-ROM (CD-R or CD-RW), an, a DVD (Digital Versatile Disk), a memory card or the like instead of the FD. The display displays data such as a document, an image and functional information, including a cursor, an icon and/or a toolbox, for example. The display may be a CRT, a TFT liquid crystal display, or a plasma display, for example. The I/F may be connected to the network such as the Internet via a communication line and is connected to other machines over the network. The I/F takes charge of an internal interface with the network and controls the input/output of data from/to an external machine. A modem or a LAN adapter, for example, may be adopted as the I/F. The keyboard includes keys for inputting letters, numbers and commands and is used to input data. The keyboard may be a touch-panel input pad or a numerical keypad. The mouse is used to move a cursor to select a range to move or change the size of a window. A trackball or joystick, for example, may be used as a pointing device if it has the same functions.

Reference Signatures

Systems of the invention include a pattern recognition unit that can compare the obtained tissue signature to a reference signature, thereby detecting the condition (such as an frequency dependent electrical impedance change which changes with time).

For tracking electrical impedance changes in tissues to diagnose a disease, it has been discovered that impedance signatures for conditions are the same across different mammals (and/or that the trends in tissue characteristics seen from tissue injuries, tissue pathologies, or tissue modifications are similar across different species). For example, the electrical impedance signature obtained from rat tissue that has been subject to a traumatic brain injury will demonstrate the same characteristic changes in the impedance signature obtained from human tissue that has been subject to the same type of traumatic brain injury (the way in which the tissue changes across species to an injury primarily depends on the tissue and injury type (not the species from which the recordings are made), and although the way in which applied electromagnetic energy distributes across a species is dependent on the geometry and tissue distribution in the species being investigated, the way in which the electromagnetic impedance tissue changes effect the energy distributions is the same across species). In methods of the invention, the obtained signatures for different conditions are used as reference signatures, e.g., the impedance signature obtained from rat tissue subject to a traumatic brain injury is a reference signature for traumatic brain injuries and the impedance signature obtained from rat tissue subject to a stroke is a reference signature for strokes. An entire database of different signatures for different conditions can be constructed and used as a reference database. An impedance signature can then be obtained from a region of tissue suspected to be associated with a condition, and that signature can be compared to the obtained reference signatures. A match between the test signature and the reference signature provides a diagnosis of the condition.

Methods for inflicting both mild and severe traumatic brain injury, e.g. mild and severe concussions, are shown in McIntosh et al. (Neuroscience, 28(1):233-244, 1989) and Sanders et al. (Brain Res 904(1):141-144, 2001), the content of each of which is incorporated by reference herein in its entirety. Such injuries of varying severity can be inflicted on rat brain tissue and impedance change over time can be measured to obtain impedance signatures for traumatic brain injuries of differing severities. The time period need only be long enough to record an impedance change in the tissue. Exemplary time periods can be multiple measurements over a few seconds, to every 30 seconds, to every 1 minute, to every 10 minutes, to every 20 minutes, to every 30 minutes, to every hour, to every couple of hours, to every day, etc.

Methods for inducing cancers in animals, e.g., mice and rats, are known in the art. The Stanford University Medical Center, Cancer Service (Stanford, Calif. 94305) offers commercially available services for inducing different cancers in animals for use in modeling cancers for diagnosis. Different cancers can be induced in different tissues of an animal and impedance change over time can be measured to obtain impedance signatures for different cancers. The time period need only be long enough to record an impedance change in the tissue. Exemplary time periods can be multiple measurements over a few seconds, to every 30 seconds, to every 1 minute, to every 10 minutes, to every 20 minutes, to every 30 minutes, to every hour, to every couple of hours, to every day, etc.

Methods of inducing strokes in animals are shown in Beech et al. (Brain Res 895(1-2):18-24, 2001), Carmichael (NeuroRx, 2(3): 396-409, 2005), Chen (Stroke, 17(4): 738-743, 1986), Graham et al. (Comp Med, 54(5): 486-496, 2004), and Watson et al. (Ann Neurol, 17(5):497-504, 1985), the content of each of which is incorporated by reference herein in its entirety. Strokes of varying severity can be induced in animal brain tissue and impedance change over time can be measured to obtain impedance signatures for strokes of differing severities. The time period need only be long enough to record an impedance change in the tissue. Exemplary time periods can be multiple measurements over a few seconds, to every 30 seconds, to every 1 minute, to every 10 minutes, to every 20 minutes, to every 30 minutes, to every hour, to every couple of hours, to every day, etc.

Methods of inducing myocardial infarctions in animals are shown in Peukurt et al. (Int J Cardiovasc Imaging, (5):529-535, 2009), the content of each of which is incorporated by reference herein in its entirety. Myocardial infarctions of varying severity can be induced in animal heart tissue and impedance change over time can be measured to obtain impedance signatures for myocardial infarctions of differing severities. The time period need only be long enough to record an impedance change in the tissue. Exemplary time periods can be multiple measurements over a few seconds, to every 30 seconds, to every 1 minute, to every 10 minutes, to every 20 minutes, to every 30 minutes, to every hour, to every couple of hours, to every day, etc.

Furthermore, the methods outlined herein could be used in the species under examination, such as humans, where a known condition is investigated across a sample of patients and the characteristics of the disease are statistically analyzed (such as with methods described in Statistics, 11th Edition by James T. McClave, Terry Sincich and William Mendenhall (2008)) and used to form a database of tissue characteristics based on a disease diagnosis and progression. This method of establishing the database of tissue characteristics, based on patients with a known condition, can be used to establish long-term disease characteristics, or used in the acute to chronic periods (from sub second to months to years in time periods).

Typical signatures comparisons of tissue characteristics are based on an analysis of tissue(s): at a single time point (compared to a single reference signature or an earlier recording), at multiple time points (compared to a multiple reference signatures or earlier recordings), to a trend in the change in tissue characteristic being investigated over multiple time points (compared to a reference signature at multiple time points demonstrating its own trend), and/or any combination. For example, a tissue characteristic can be recorded from an individual being followed, and the change in tissue characteristics from their baseline measurements can be used as the diagnostic information, as it can form a unique signature of the disease (for example, in the acute period following injury the electromagnetic impedance of a tissue shows a particular signature, such as a change in complex impedance amplitude and phase as functions of time post injury and frequency, which can be used to diagnose a disease).

Incorporation with Other Diagnostics and/or Treatment Methods

The methods/device outlined herein can be extended to work with and/or integrated with other diagnostic measures and/or diagnostic tools (either through feedback control methods or passive monitoring methods), such as imaging modalities, physiological monitoring methods/devices, diagnostic methods/devices, and biofeedback methods/devices (either a person performing an exam or an automated device) (such as those described in co-owned and co-pending U.S. patent application Ser. No. 13/162,047, the content of which is incorporated by reference herein in its entirety), where the referenced work describes the application of energies for brain stimulation, but the modification would be made from the referenced work to use the energy sources for determining the tissue characteristics as outlined herein. The measurements made from these other devices/methods can be correlated with the unique signatures we outline and describe herein to provide an additional level of diagnostic information.

For example for diagnosing TBI or stroke, one could integrate this method with methods to measure biomarkers indicative of tissue injury (such as could be sampled from body tissue such as fluids whereby markers of brain damage can be sampled in the blood, cerebral spinal fluid, saliva, or other body fluid), integrated with electrophysiological measurements (such as an EEG recording that simultaneously evaluates changes in brain activity where electrical activity from the brain can demonstrate changes indicative of injury), ocular measurements (such as measuring changes in eye behavior following injury or taking measurements of ICP (which can also be made from other locations, but is classically thought of as being a ocular measurement) where for example one could follow simultaneous measurements of ICP and changes in brain tissue impedance as a function of time to determine if a patient had a mild or severe form of TBI, balance testing (where brain injury is commonly associated with changes in balance), assessing the sensory system (where for example changes in the olfactory, auditory, tactile, and/or visual systems can be correlated to and/or used to predict with brain injury), and/or cognitive evaluations (such as those made by a physician (or even those made by an automated system)). The measurements that we describe herein based on measured energy characteristics in a tissue can furthermore be sued to predict these other markers or measurements that are used to predict tissue injury, such as for example measuring tissue impedance changes to predict changes in ICP.

Furthermore, the transduction and/or measurement mechanisms described herein can be integrated with any other device using the same transduction and/or measurement mechanisms for other purposes, such as for example using the electrodes for an EEG system as part of the means to investigate the change in electromagnetic impedance in the a head of a patient being investigated (this could be used with any bio-potential measurement system (described in Medical Instrumentation Application and Design by John G. Webster (Feb. 3, 2009) or Principles of Applied Biomedical Instrumentation by L. A. Geddes and L. E. Baker (1989))). Furthermore for imaging, the energies that are applied to the tissues for characterizing properties of the tissue for disease diagnosis (such as those used to investigate changes in impedance properties of the tissue as a function of frequency and/or time) could have a dual use in imaging the tissue (such as for example energy from an ultrasound for classical imaging could be used to investigate impedance changes in the tissue as outlined herein (electrical and/or mechanical impedance changes)).

The methods/device outlined herein can be extended to work with and/or integrated with other therapeutic methods or device (either through feedback control methods or passive monitoring methods), such for example with brain stimulation devices, such as those outlined and explained in (Wagner et al, U.S. patent application Ser. No. 13/102,476) whereby these methods herein could be integrated with methods that control dosing and targeting (Such as Wagner et al, U.S. patent application Ser. No. 13/216,282).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Systems of the invention make impedance measurements that are recorded not at a single frequency, but at multiple frequencies; examine tissue capacitance (permittivity) as well as tissue resistance (conductivity); and track tissue changes as a function of time and frequency. This is done to generate a spectral "finger print" (i.e., impedance signature of specific behavior of tissue as function of frequency and/or time). Systems of the invention can be used with any pathology where tissue impedances change as a function of pathology, time, and/or frequency. Systems of the invention allow for development of a library of tissue behaviors that can be used to diagnose pathologies and discriminate between different pathologies.

Example 1

Detecting Strokes

According to the World Health Organization over 15 million people per year suffer strokes. Of those, 5 million perish and another 5 million are left permanently disabled. A popular misconception is that stroke is a disease of affluent nations; epidemiological data proves otherwise, as over 60% of stroke deaths are attributed to low-income developing countries. There are a number of reasons for this discrepancy. But stroke survival and recovery can be drastically improved by rapid diagnosis and classification. This is often impossible in underdeveloped countries due to the lack of low cost imaging and/or diagnostics.

Systems of the invention offer a low cost noninvasive way to identify and classify strokes based on changes in brain impedance. Systems of the invention are capable of identifying the stroke type, the time of injury onset, and the extent of the injury via external multi-channel, multi-frequency, measurements of the head impedance network (resistance and capacitance of scalp-skull-cerebral spinal fluid-brain tissue). Low intensity currents are injected across the scalp. Although the currents have negligible physiological effect, they call be used to measure tissue properties, while being completely safe. Field distributions in the brain are drastically different between stroke and non-stroke cases. This is a result of changes in the tissue impedance measurements. Ultimately these differences manifest via different voltage distributions that can be measured at the skin surface. Systems of the invention can measure DC resistance ($\alpha 1/\sigma$, conductivity), frequency ($\omega$, Field frequency), dependent resistance ($\alpha 1/\sigma$) and capacitance ($\alpha 1/\in$, permittivity). FIG. 2 shows that potential differences in tissue conductivity and permittivity are dependent on type and severity of injury (based on measurements that were made in the brains of cats that underwent tissue injury). Additionally, the time course of the injury has a frequency dependent behavior, which demonstrates spectral signatures that can be tracked from surface impedance recordings. This data serves to guide noninvasive impedance measurements, and predict stroke characteristics. The data were recorded during neurosurgeries in animals at low frequencies (<10 kHz).

Reference Signature

60 Sprague Dawley rats are randomly divided into 3 separate subgroups (control, ischemic stroke, and hemorrhagic stroke). The rats are anaesthetized, placed in a stereotactic frame, and then have their skin, muscle, skull, CSF, gray matter, and white matter surgically exposed and investigated with a 4 pronged modified micro-controlled platinum coated stainless steel forceps device connected to an impedance analyzer (Hewlett Packard, HP4192A, Palo Alto). For each rat and tissue, measurements are made from 10 to 50,000 Hz at 5 Hz steps, with approximately 10 sweeps per tissue (at unique locations) and averaged. As the dimensions of the recording probe are micro-controlled, the permittivity and conductivity is determined from the measured impedances, with methods similar to those demonstrated in (Hart, F. X., Toll, R. B., Berner, N. J., & Bennett, N. H., The low frequency dielectric properties of octopus arm muscle measured in vivo. *Phys. Med. Biol.* 41, 2043-2052 (1996)) or (Foster, K. R. & Schwan, H. P., Dielectric Properties of Tissues in *Biological Effects of Electromagnetic Fields*, edited by C. Polk & E. Postow (CRC Press, New York, 1996), pp. 25-102) or (Dielectric Properties of body tissues in the frequency range of 10 Hz to 100 GHz—Work reported from the Brooks Air Force Base Report "Compilation of the dielectric properties of body tissues at RF and microwave frequencies" by C. Gabriel. (2007).). Once baseline recordings are taken, animals in the ischemic group have a large ischemic stroke induced in one hemisphere (ischemia is maintained throughout the protocol), animals in the hemorrhagic group have a large hemorrhagic stroke induced in one hemisphere, and the controls have their tissues maintained. The animals then have their brain tissue impedances monitored at ten-minute intervals over an 8-hour period (time period chosen to be greater than the acute stroke treatment decision window), in both the right and left hemispheres (to also include in-animal controls).

The results from the tissue recordings, from all of the tissues, are fed into human based MRI guided finite element models (FEM) developed with Ansoft Maxwell (Pittsburg, Pa.) and Matlab (Natick, Mass.) software. The FEM models the effects of low frequency, electrode driven constant currents, that are evaluated as surface voltages at paired recording electrode locations based on electroquasistatic models of tissue behavior, solving specially for sinusoidal steady state solutions of:

$$\nabla \cdot (j\omega \in \nabla\Phi + \sigma \nabla\Phi) = 0$$

where $\Phi$ (voltage) is the negative divergence of the electric field in the tissues, $\sigma$ is the tissue conductivity, $\in$ the tissue permittivity, $\omega$ the field frequency. These models are used to analyze how stroke induced changes in brain tissue impedance affect surface voltage recordings, determine recording resolution as a function of recording/stimulating electrode size and number, establish measurable depth and size of a stroke injury, and allow for capability to discriminate the stroke time course.

Detecting a Stroke

A system as shown in FIG. 3 may be used to measure impedance change in tissue. Electrodes are connected to different areas of a person's head. A constant current source at a particular frequency is applied to the tissues via surface electrodes, such as those placed on the scalp. Along the same electrodes (or separate electrodes in approximately the same scalp region) voltage measurements are made across the region of scalp and underlying brain tissue. These obtained values are used to calculate impedance:

$$Z(\omega) = V(\omega)/I(\omega)$$

where the impedance (Z) is a function of the frequency ($\omega$), and will have an amplitude and a phase relative to the constant current or voltage input. The impedance, $Z(\omega)$, is determined by the calculation of $V(\omega)/I(\omega)$ at any time point, t. The impedance may be tracked as a function of time, for any frequency, $\omega$. One can make these measurements at multiple frequencies (such as through stepping through multiple frequencies at different time points or applying multiple frequencies at one time (at the same or different electrodes)). One can measure and track changes in the conductivity and permittivity by assuming that the head under study has a defined geometry under the recording electrodes (where $Z(\omega) = [R(\omega) \times (1/(j\omega C(\omega)))]/[R(\omega) + (1/(j\omega C(\omega)))]$, and R (resistance) and C (capacitance) are also functions of geometry, and can be calculated based on the electrode positions and/or size, and the head properties).

The process is repeated multiple times to obtain a measure of impedance change over time, i.e., an impedance signature. The obtained impedance signature is compared to the obtained reference impedance signatures. A match between the obtained impedance signature from the person and one of the reference signatures indicates that the person has suffered a stroke. The severity of the stroke is also determined based upon which reference signature matches the obtained signature.

Example 2

Detecting Traumatic Brain Injuries

Traumatic brain injury (TBI), such as concussions, affects over 1.6 million Americans every year. The diagnosis of mild or moderate closed head traumatic brain injuries is particularly challenging due to poor diagnostic criteria and the lack of portable neurodiagnostic devices that can rapidly detect changes in brain tissue after non-penetrating head trauma. The diagnosis of mild closed head traumatic brain injuries is particularly challenging due to poor diagnostic criteria. Although mild TBI patients suffer numerous cognitive deficits, diagnosis via cognitive assessments are difficult because full cognitive symptoms might not manifest for days post-injury. Additionally, assessments often require pre-injury baselines for definitive diagnoses, and automated methods are underdeveloped. Systems of the invention allow for diagnosis and classification of TBI.

Reference Signature

60 Sprague Dawley rats are randomly divided into 3 subgroups (those receiving: mild closed head TBI (n=20), severe closed head TBI (n=20), and uninjured controls (n=20)). Mild TBI is generated using the mild lateral fluid percussion injury (LFPI) protocol (1.4-1.5 atm). Severe TBI will be generated with a major lateral fluid percussion injury (LFPI) protocol (3.0-3.5 atm). LFPI results in a reproducible cortical injury leading to approximately 1 mm-deep patchy neuronal death over the exposed 3 mm diameter surface area. Further details on the method are available in McIntosh et al. (Neuroscience, 28(1):233-244, 1989) and Sanders et al. (Brain Res 904(1):141-144, 2001).

In half of the rats, brain tissue impedances (from 10 to 50,000 Hz in logarithmic steps) will be directly investigated with a 4 pronged micro-controlled forceps impedance probe connected to an Electrical Impedance Tomography (EIT) device based on circuitry of an HP4192A impedance analyzer (Wagner, T. (2006). Non Invasive Brain Stimulation: Modeling and Experimental Analysis of Transcranial Magnetic Stimulation and Transcranial DC Stimulation as a Modality for Neuropathology Treatment Health Sciences and Technology. Cambridge, MIT/Harvard Medical School. PhD: 249) in conjunction with a National Instruments Lab View control system. The probe is fabricated from two self-closing forceps mechanisms (Dumont N5) for use as a controllable, four plate probe. Probe tips are coated under high vacuum conditions (5×10−7 ton) with 10 nm Titanium (99.99% Alfa Aesar) as an adhesion layer followed by 50 nm of Platinum (99.99% Alfa Aesar). The tips are then re-attached to the closing mechanism using four plastic adapter plates, providing electrical insulation from proximal instruments and tissues. The self-closing handle mechanism is also modified using two fine-threaded screws to allow for precise and repeatable control of the inter-electrode separation distance.

Further control is achieved by fixing the impedance probe to a micro positioner (Kopf, Tujunga, Calif.). Overall, tissue volume is maintained constant at 50 µm×200 µm×400 µm (+/−10 µm per dimension). These measurements are done invasively during surgical procedures. For these invasive recordings, recordings are taken from the cerebral cortex directly at the site of injury and at locations +/−2 and 4 mm from the injury site (in addition to the cortical tissues, recordings are also taken from the exposed bone and reflected skin). The other half of the animals are evaluated noninvasively via scalp surface measurements. These recordings are done with modified EEG electrodes (5 mm×5 mm) attached via conducting paste (Elefix). The noninvasive recordings are made across 6 channels on the rat head, with 25 $mm^2$ electrodes placed 2, 4, and 6 mm bilaterally from the interaural line (3 per hemisphere). In both groups, tissue impedances is monitored at twenty-minute intervals over an 8-hour period (to extend past typical acute injury time windows), where specifically the complex impedances is recorded (i.e., magnitude and phase angle as a function of time and tissue type).

The invasive recordings allow for development of a direct measure of the permittivity and conductivity of the tissues (as the dimensions of the probe are fixed, allowing a reconstruction of tissue parameters similar to Hart et al. (Phys. Med. Biol. 4:2043-2052, 1996). The noninvasive measures allows for assessment of the impedance changes of the full tissue network as measured across the scalp (and correlated with the invasive measures, provides an empirical measure between individual tissue injury, assessed at the tissue, and those measured at the scalp).

Impedance changes are recorded (complex magnitude and angle) as a function of injury type, location relative to injury focus, tissue type, and time (from time of injury to 8 hours post) in 60 Sprague Dawley rats (20 mild TBI, 20 severe TBI, and 20 controls (split evenly between invasive and noninvasive measures)).

The results from the tissue recordings are analyzed to establish time dependent spectral signature differences between different injuries and correlate between the invasive and noninvasive recordings. This is completed via mathematical analysis of the invasive and noninvasive recordings and EIT simulations developed with MRI guided finite element models based on the invasive recordings. This modeling process takes place throughout the duration of the protocol, continually building on the empirical data measurements for the different conditions explored (i.e., mild TBI, severe TBI, and uninjured tissue recorded both invasively and noninvasively), allowing for an optimized computational model.

The results from the invasive measurements (i.e., tissue conductivity and permittivity averaged across individual conditions) are fed into a MRI guided, finite element model (FEM) of the tissue bioimpedance of the rat head and brain, developed with Ansoft Maxwell and Matlab software, to determine the effect of the different traumatic brain injuries on the injected currents during EIT and the resulting bioimpedance measurements. Sinusoidal steady solutions of the electromagnetic field distributions are developed for each frequency point analyzed (i.e., between 0.01 to 50 kHz), and modeled at each of the individual time points when measurements are made (i.e., between time zero and the 8 hour point), with simulated field sources representing the noninvasive surface EIT electrodes (i.e., from the 6 surface 25 $mm^2$ electrodes on the rat scalp). Further detail regarding the computational methods is shown in Wagner et al. (IEEE Trans Biomed Eng, 51(9):1586-98, 2004) and Wagner et al. (Neuroimage, 35(3):1113-24, 2007). The modeling process allows for determination of a simulated noninvasive complex impedance measurement (by dividing the resulting complex voltage by the injected current at the surface electrode contact), and prediction of the effects as a function of time following the injury (by comparing results across models constructed for different time points).

The simulated predictions are then compared to the empirical data gathered during the invasive and noninvasive measurements to optimize the computational tissue model (and EIT prediction), and specifically identify key features of the impedance perturbations as a function of injury severity, tissue type, time post injury, and EIT signal frequency (i.e., filtering effects of the injured tissues on the injected EIT currents through the spectral analysis of the resulting EIT fields). During simulation, optimal EIT electrode shape, placement, and number relative to the injury type/location is determined. This allows for correlation of the injury type and severity with the electromagnetic measures taken both invasively and noninvasively.

The resulting analysis provides models of both human and rat head/brains for mild TBI, severe TBI, and healthy conditions based on empirical impedance recordings, and thus provides a reference signature to predict EIT surface recordings as a function of injury severity, tissue type, time post injury, and EIT signal frequency.

Detecting a Traumatic Brain Injury

A system as shown in FIG. 3 may be used to measure impedance change in tissue. Electrodes are connected to different areas of a person's head. A constant current source at a particular frequency is applied to the tissues via surface electrodes, such as those placed on the scalp. Along the same electrodes (or separate electrodes in approximately the same scalp region) voltage measurements are made across the region of scalp and underlying brain tissue. These obtained values are used to calculate impedance:

$$Z(\omega)=V(\omega)/I(\omega)$$

where the impedance (Z) is a function of the frequency ($\omega$), and will have an amplitude and a phase relative to the constant current or voltage input. The impedance, $Z(\omega)$, is determined by the calculation of $V(\omega)/I(\omega)$ at any time point, t. The impedance may be tracked as a function of time, for any frequency, $\omega$. One can make these measurements at multiple frequencies (such as through stepping through multiple frequencies at different time points or applying multiple frequencies at one time (at the same or different electrodes)). One can measure and track changes in the conductivity and permittivity by assuming that the head under study has a defined geometry under the recording electrodes (where $Z(\omega)=[R(\omega)\times(1/(j\omega C(\omega)))]/[R(\omega)+(1/(j\omega C(\omega)))]$, and R (resistance) and C (capacitance) are also functions of geometry, and can be calculated based on the electrode positions and/or size, and the head properties).

The process is repeated multiple times to obtain a measure of impedance change over time, i.e., an impedance signature. The obtained impedance signature is compared to the obtained reference impedance signatures. A match between the obtained impedance signature from the person and one of the reference signatures indicates that the person has suffered a traumatic brain injury. The severity of the traumatic brain injury is also determined based upon which reference signature matches the obtained signature.

What is claimed is:

1. A system for monitoring tissue and detecting a condition, the system comprising:
   at least one energy source configured to output to a tissue an energy field comprising a fixed energy component at a pre-determined frequency;
   a transduction unit configured to:
      receive a signal from the tissue over multiple time points;
      generate a first impedance value at a first time point by determining a correlation at the first time point between the output of the fixed energy component at the pre-determined frequency and the received signal from the tissue at the first time point;
      generate a second impedance value at a second time point by determining a correlation at the second time point between the output of the fixed energy component at the pre-determined frequency and the received signal from the tissue at the second time point; and
      generate an impedance signature that is representative of a change in the first impedance value at the first time point and the second impedance value at the second time point; and
   a pattern recognition component that compares the impedance signature generated by the transduction unit with a database of one or more impedance signatures of a traumatic brain injury.

2. The system according to claim 1, wherein the energy source is an electric source that produces an electric field.

3. The system according to claim 2, wherein the electric field is pulsed.

4. The system according to claim 2, wherein the electric field is time varying.

5. The system according to claim 2, wherein the electric field is pulsed a plurality of time, and each pulse may be for a different length of time.

6. The system according to claim 2, wherein the electric field is time invariant.

7. The system according to claim 2, wherein the electric source is at least one electrode.

8. The system according to claim 1, wherein the energy source and the transduction unit are integrated with each other.

9. The system according to claim 7, wherein the electrode may be a component of a second system selected from the group consisting of: EEG, EKG, EOG, ERG, and ENG.

10. The system according to claim 1, wherein the system is integrated with an imaging system.

11. The system according to claim 1, wherein the energy source is selected from the group consisting of: electromagnetic, chemical, optical, thermal, mechanical, and a combination thereof.

12. The system according to claim 11, wherein the mechanical field is generated by an ultrasound device.

13. A system for monitoring tissue and detecting a condition, the system comprising:
   an electric source that produces an electric field at a fixed current a pre-determined frequency;
   an electrical transduction unit configured to:
      receive a signal from the tissue over multiple time points;
      generate a first impedance value at a first time point by determining a correlation at the first time point between the electric field at the fixed current the pre-determined frequency and the received signal from the tissue at the first time point;
      generate a second impedance value at a second time point by determining a correlation at the second time point between the electric field at the fixed current the pre-determined frequency and the received signal from the tissue at the second time point; and
      generate an impedance signature that is representative of a change in the first impedance value at the first time point and the second impedance value at the second time point; and;

a pattern recognition component that compares the impedance signature generated by the transduction unit with a database of one or more impedance signatures of a traumatic brain injury; and a helmet that houses at least the electric source or transduction unit.

14. The system according to claim 13, wherein the electrical transduction unit measures the electrical impedance of the tissue.

15. The system according to claim 13, wherein the system is integrated with a second system selected from the group consisting of: EEG, EKG, EOG, ERG, and ENG.

16. A system for monitoring tissue and detecting a condition, the system comprising:
   a noninvasive transcranial stimulator configured to output to a tissue an energy field comprising a fixed energy component at a pre-determined frequency;
   a transduction unit configured to:
      receive a signal from the tissue over multiple time points;
      generate a first impedance value at a first time point by determining a correlation at the first time point between the output of the fixed energy component at the pre-determined frequency and the received signal from the tissue at the first time point;
      generate a second impedance value at a second time point by determining a correlation at the second time point between the output of the fixed energy component at the pre-determined frequency and the received signal from the tissue at the second time point; and
      generate an impedance signature that is representative of a change in the first impedance value at the first time point and the second impedance value at the second time point; and
   a pattern recognition component that compares the impedance signature generated by the transduction unit with a database of one or more impedance signatures of a traumatic brain injury.

* * * * *